US006605707B1

(12) United States Patent
Kerdesky et al.

(10) Patent No.: US 6,605,707 B1
(45) Date of Patent: Aug. 12, 2003

(54) PROCESS FOR THE PREPARATION OF 6-O-PROPARGYL ERYTHROMYCIN DERIVATIVES

(75) Inventors: Francis A. J. Kerdesky, Grayslake, IL (US); Ramiya Premchandran, Gurnee, IL (US); Gregory S. Wayne, Vernon Hills, IL (US); Sou-Jen Chang, Prairie View, IL (US); Jonathan P. Pease, Antioch, IL (US); Lakshmi Bhagavatula, Vernon Hills, IL (US); John E. Lallaman, Zion, IL (US); Howard E. Morton, Gurnee, IL (US); Steven A. King, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/533,703

(22) Filed: Mar. 23, 2000

(51) Int. Cl.$^7$ ................................................ C07H 1/00
(52) U.S. Cl. ........................ 536/7.4; 536/7.2; 536/18.5
(58) Field of Search ......................... 536/7.2, 7.5, 18.5

(56) References Cited

U.S. PATENT DOCUMENTS

| 3,780,028 A | 12/1973 | Naita |
|---|---|---|
| 4,331,803 A | 5/1982 | Watanabe et al. |
| 4,670,549 A | 6/1987 | Morimoto et al. |
| 4,680,386 A | 7/1987 | Morimoto et al. |
| 4,990,602 A | 2/1991 | Morimoto et al. |
| 5,866,549 A | 2/1999 | Or et al. |
| 5,892,008 A | 4/1999 | Ku et al. |
| 5,929,219 A | 7/1999 | Hill |

FOREIGN PATENT DOCUMENTS

| DE | 1966310 | 8/1969 |
|---|---|---|
| WO | 97 42204 | 11/1997 |
| WO | 99 21871 | 5/1999 |

OTHER PUBLICATIONS

J. Am. Chem. Soc., 78, 388–395 (1956).

J. Org. Chem., 53, 2340 (1988).

"Comprehensive Organic Transformation. A Guide to Functional Group Preparations", VCH Publishers, NY (1989).

*Primary Examiner*—Elli Peselev
(74) *Attorney, Agent, or Firm*—B Gregory Donner

(57) ABSTRACT

Disclosed herein is a process for the preparation of erythromycin derivatives, or pharmaceutically acceptable salts thereof, which contain an optionally substituted propargyl group at the 6-O-position.

36 Claims, No Drawings

PROCESS FOR THE PREPARATION OF 6-O-PROPARGYL ERYTHROMYCIN DERIVATIVES

TECHNICAL FIELD

The instant invention relates to a process for the preparation of erythromycin derivatives, or pharmaceutically acceptable salts thereof, which contain an optionally substituted propargyl group at the 6-O-position.

BACKGROUND OF THE INVENTION

Macrolide antibacterial agents are widely used to treat and prevent bacterial infections. However, the discovery of bacterial strains which have resistance or insufficient susceptibility to these agents has promoted development of compounds with modified or improved profiles of antibiotic activity.

Commonly owned U.S. Pat. No. 5,866,549 and commonly owned pending U.S. application Ser. No. 09/273,140, filed Mar. 19, 1999, teach the small scale syntheses of 6-O-propargyl erythromycin derivatives. Large scale production of the same, however, requires a process which avoids complicating factors such as chromatography of intermediates and low-yielding steps, i.e., problems usually associated with macrolide or ketolide synthesis due to the number of reactive groups on the molecule.

Therefore, there is still a continuing need for more efficient and cleaner syntheses of 6-O-propargyl erythromycin derivatives.

SUMMARY OF THE INVENTION

In one embodiment of the instant invention, therefore, is disclosed a process for preparing 6-O-propargyl erythromycin derivatives, or a pharmaceutically acceptable salts thereof, comprising the steps of (a) simultaneously reacting a compound of formula (I)

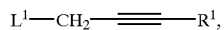

(I)

wherein
$L^1$ is selected from the group consisting of halo, trifluoromethanesulfonyl, and optionally substituted phenylsulfonyl; and
$R^1$ is hydrogen or optionally substituted heteroaryl, a compound of formula (II)

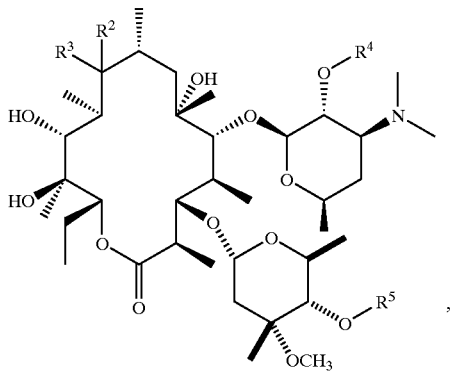

(II)

wherein
$R^2$ and $R^3$ are taken together and are selected from the group consisting of $=N-O-R^6$, $=N-O-C(O)-R^6$, $=N-O-C(R^{7a})(R^{7b})-OR^8$, $=N-O-Si(R^9)_3$, $=N-N(R^{10a})(R^{10b})$, and $=N-N=C(R^{11a})(R^{11b})$;

$R^4$ and $R^5$ are independently hydrogen or a hydroxyl protecting group;
$R^6$ is selected from the group consisting of alkyl, cycloalkyl, cycloalkylalkyl, phenyl, and phenylalkyl;
$R^{7a}$ and $R^{7b}$ are independently selected from the group consisting of hydrogen, alkyl, cycloalkyl, cycloalkylalkyl, phenyl, and phenylalkyl;
$R^8$ is selected from the group consisting of alkyl, cycloalkyl, cycloalkylalkyl, phenyl, and phenylalkyl; or
$R^{7a}$ and $R^{7b}$ together or $R^{7a}$ and $R^{7b}$ together are alkylene; each $R^9$ is independently selected from the group consisting of alkyl, cycloalkyl, cycloalkylalkyl, phenyl, and phenylalkyl;
$R^{10a}$ and $R^{10b}$ are independently selected from the group consisting of alkyl, cycloalkyl, cycloalkylalkyl, phenyl, phenylalkyl, and a nitrogen-protecting group; or
$R^{10a}$ and $R^{10b}$ together are alkylene; and
$R^{11a}$ and $R^{11b}$ are independently selected from the group consisting of hydrogen, alkyl, cycloalkyl, cycloalkylalkyl, phenyl, and phenylalkyl; or
$R^{11a}$ and $R^{11b}$ together are alkylene, and an alkoxide base to provide a compound of formula (III)

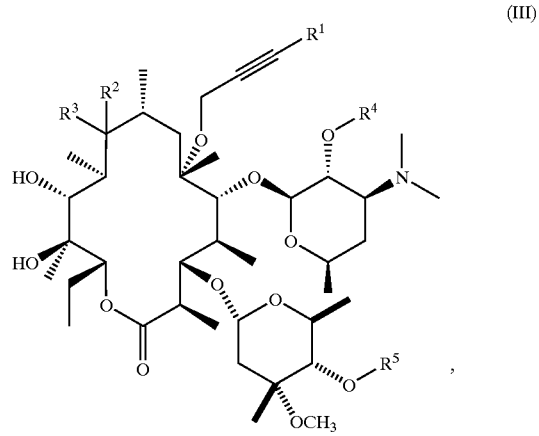

(III)

a preferred embodiment of which are compounds of formula (III-a)

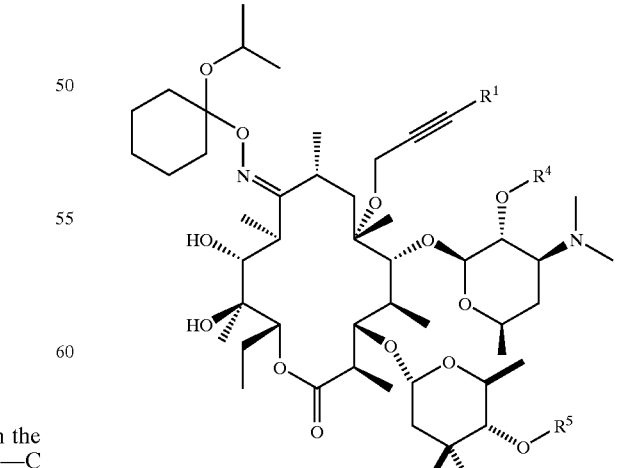

(III-a)

and
a particularly preferred embodiment of which are compounds of formula (III-b)

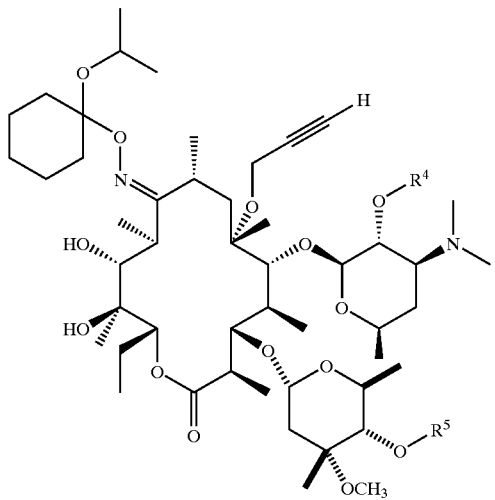
(III-b)

Compounds of formula (III) are useful as intermediates in the synthesis of 6-O-propargyl erythromycin derivatives of formula (IV)

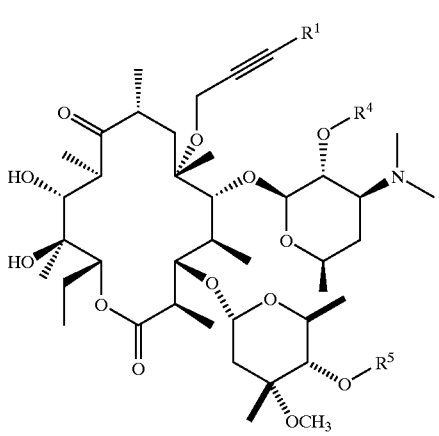
(IV)

a preferred embodiment of which are compounds of formula (IV-a)

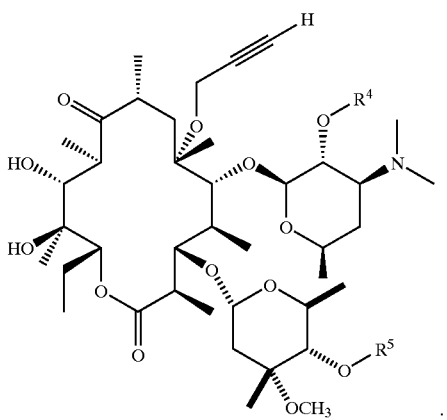
(IV-a)

Another embodiment of the instant invention, therefore, comprises the step of
(a) reacting the compound of formula (III) with a first acid and sodium nitrite at a pressure of about 15 psi to about 70 psi to provide the compound of formula (IV).

Compounds of formula (IV) are useful as intermediates in the synthesis of 6-O-propargyl erythromycin derivatives of formula (V)

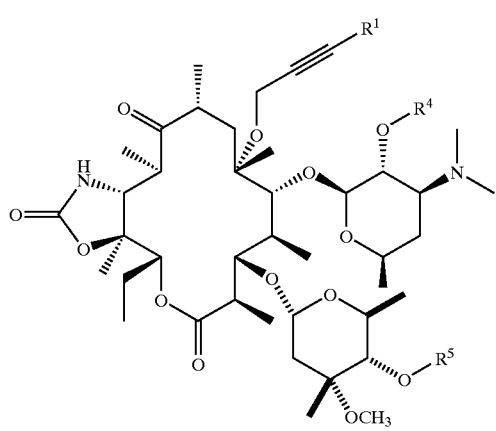
(V)

a preferred embodiment of which are compounds of formula (V-a)

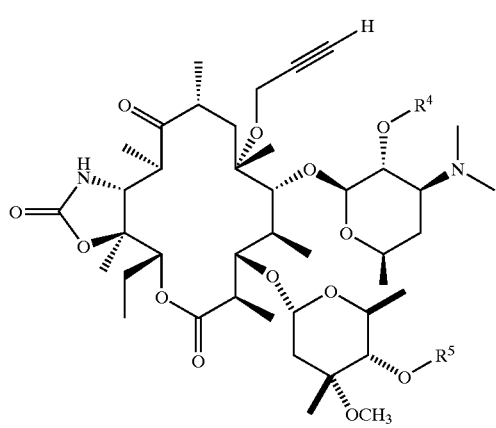
(V-a)

and
compounds of formula (V-b)

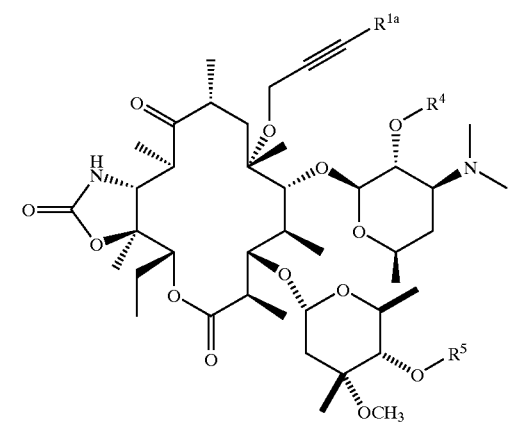
(V-b)

wherein

R$^{1a}$ is optionally substituted heteroaryl, and a particularly preferred embodiment of which are compounds of formula (V-c)

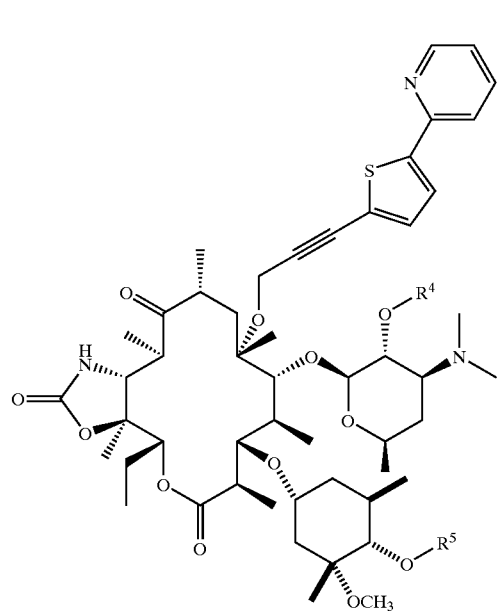

Another embodiment of the instant invention, therefore, comprises the steps of (a) reacting the compound of formula (IV-a) with 1,1'-carbonyldiimidazole and a first base, followed by treatment of the product with ammonia or ammonium hydroxide and a second base to provide the compound of formula (V-a); and (b) optionally reacting the product of step (a) with a compound of formula L$^1$—R$^{1a}$, a palladium catalyst, an additive, and the first base, to provide the compound of formula (V-b).

Compounds of formulas (V) are useful as intermediates in the synthesis of 6-O-propargyl erythromycin derivatives of formula (VII)

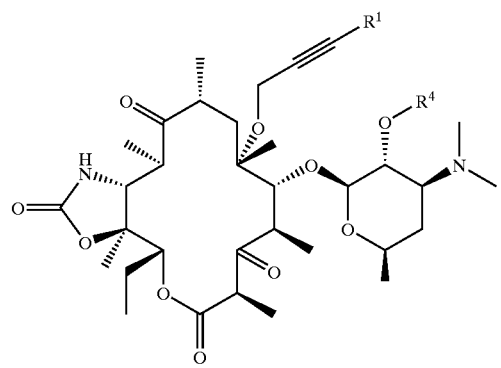

preferred embodiments of which are compounds of formula (VII-a)

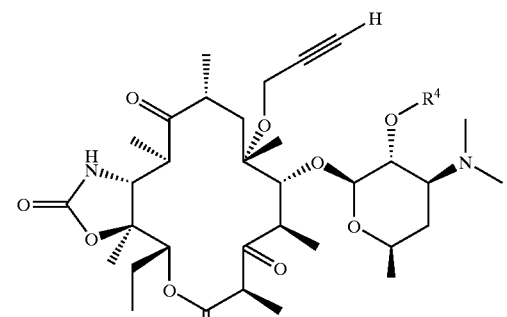

compounds of formula (VII-b),

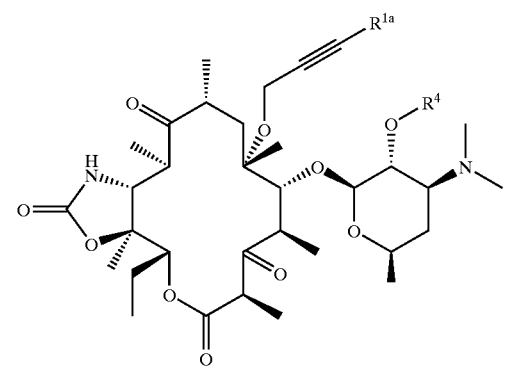

and compounds of formula (VII-c)

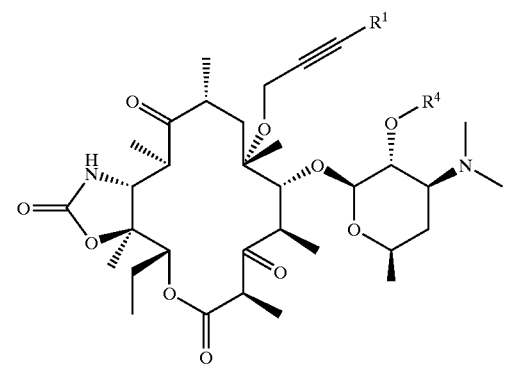

and a particularly preferred embodiment of which are compounds of formula (VII-d)

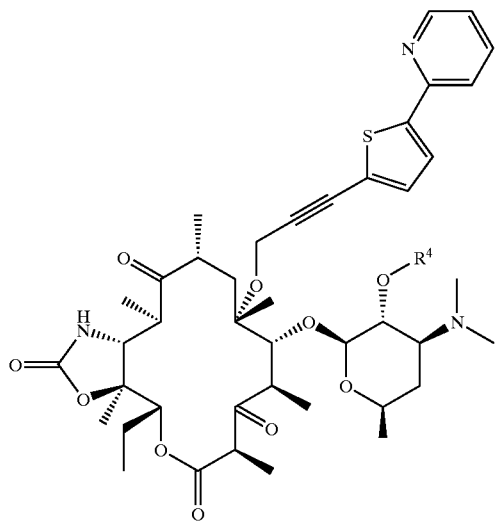

(VII-d)

Another embodiment of the instant invention, therefore, comprises the steps of (a) reacting the compound of formula (V) with a second acid to provide a compound of formula (VI)

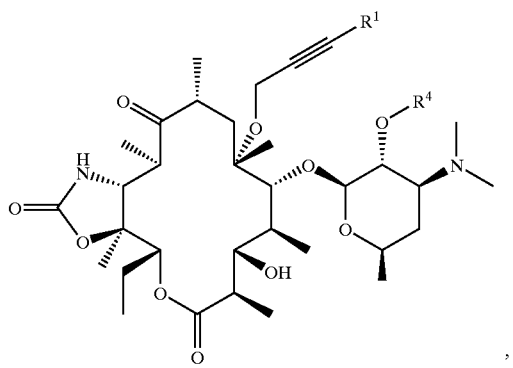

(VI)

a particularly preferred embodiment of which are compounds of formula (VI-a)

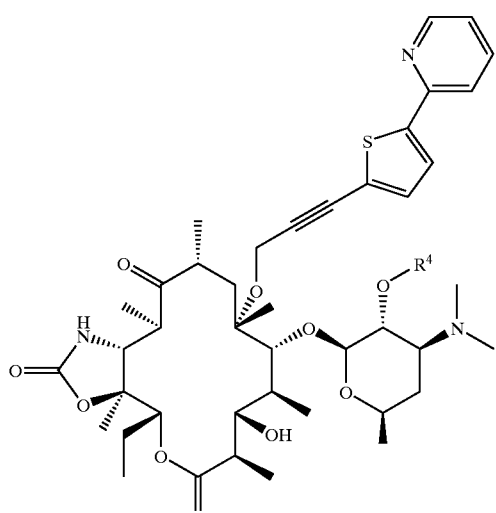

(VI-a)

(b) reacting the product of step (a) with an oxidizing agent to provide the compound of formula (VII);

(c) optionally reacting the product of step (b) with the compound of formula $L^1$—$R^{1a}$, the palladium catalyst, the additive, and the first base; and (d) optionally deprotecting the product of step (b) or step (c) to provide the compound of formula (VII-c).

In a particularly preferred embodiment of the instant invention, $L^1$—$R^{1a}$ is 2-(5-bromo-2-thienyl)pyridine.

Another embodiment of the instant invention, therefore, comprises the step of (a) reacting 2-(2-thienyl)pyridine and N-bromosuccinimide.

DETAILED DESCRIPTION OF THE INVENTION

The instant invention discloses a method for the synthesis of 6-O-propargyl erythromycin derivatives. As used in the specification, the following have the meanings indicated.

The term "additive," as used herein, refers to monodentate phosphorus-containing ligands of formulas $P(R^C)_3$ (phosphines) and $P(OR^D)_3$ (phosphites), wherein each $R^C$ is independently hydrogen; alkyl such as methyl, ethyl, and tert-butyl; cycloalkyl such as cyclopropyl and cyclohexyl; optionally substituted aryl such as phenyl, naphthyl, and ortho-tolyl; and optionally substitted heteroaryl such as furyl and pyridyl; and wherein each $R^D$ is independently alkyl such as methyl, ethyl, and tert-butyl; cycloalkyl such as cyclopropyl and cyclohexyl; optionally substituted aryl such as phenyl, naphthyl, and ortho-tolyl; and optionally substituted heteroaryl such as furyl and pyridyl. Specific examples of these additives include tri(alkyl)phosphines such as trimethylphosphine, triethylphosphine, tributylphosphine, and the like; tri(cycloalkyl)phosphines such as tricyclopropylphosphine, tricyclohexylphosphine, and the like; tri(aryl)phosphines such as triphenylphosphine, trinaphthylphosphine, and the like; tri(heteroaryl) phosphines such as tri(fury-2-yl)phosphine, tri(pyrid-3-yl) phosphine, and the like; tri(alkyl)phosphites such as trimethylphosphite, triethylphosphite, tributylphosphite, and the like; tri(cycloalkyl)-phosphites such as tricyclopropylphosphite, tricyclohexylphosphite, and the like; tri(aryl)phosphites such as triphenylphosphite, trinaphthylphosphite, and the like; and tri(heteroaryl) phosphites such as tri(fury-2-yl]phosphite, tri(pyrid-3-yl) phosphite, and the like. The term "additive," as used herein, also refers to bidentate phosphines such as 1,4-bis (diphenylphosphino)butane (dppb), 1,2-bis(diphenylphosphino)ethane (dppe), 1,1-bis(diphenylphosphino) methane (dppm), 1,2-bis(dimethyl-phosphino)ethane (dmpe), 1,1'-bis(diphenylphosphino)ferrocene (dppf), and the like.

The term "alkoxide base," as as used herein, refers to $(M)^+(OR^1)^-$, wherein $(M)^+$ is a cation selected from the group consisting of lithium, sodium, and potassium, and $R^1$ is alkyl, as defined herein. Examples of alkoxide bases include lithium methoxide, lithium ethoxide, lithium iso-propoxide, lithium tert-butoxide sodium methoxide, sodium ethoxide, sodium iso-propoxide, sodium tert-butoxide, potassium methoxide, potassium ethoxide, potassium iso-propoxide, potassium tert-butoxide, and the like.

The term "alkyl," as used herein, refers to a saturated, monovalent straight or branched chain hydrocarbon having from one to six carbons. Examples of alkyls are methyl, ethyl, propyl, isopropyl, butyl, tert-butyl, and the like.

The term "alkylsulfonyl," as used herein, refers to an alkyl group, as defined herein, attached to the parent molecular group through a sulfonyl, as defined herein.

The term "alkylene," as used herein, refers to a divalent straight or branched chain saturated hydrocarbon diradical having from one to six carbons. Examples of alkylenes are ethylene, propylene, butylene, pentylene, hexylene, and the like.

The term "alkynyl," as used herein, refers to a monovalent straight or branched chain hydrocarbon group having from two to six carbons and at least one carbon-carbon triple bond.

The term "amino," as used herein, refers to —$NH_2$ or a derivative formed by independent replacement of one or both hydrogen atoms thereof with a substituent or substituents independently selected from the group consisting of alkyl, cycloalkyl, cycloalkylalkyl, phenyl, phenylalkyl, and an amino protecting group.

The term "aminosulfonyl," as used herein, refers to an amino group, as defined herein, attached to the parent molecular group through a sulfonyl group, as defined herein.

The terms "amino protecting group," or "nitrogen protecting group," as used herein, refer to selectively introducible and removable groups which protect amino groups against undesirable side reactions during synthetic procedures. Examples of amino protecting groups include methoxycarbonyl, ethoxycarbonyl, trichloroethoxycarbonyl, benzyloxycarbonyl (Cbz), chloroacetyl, trifluoroacetyl, phenylacetyl, formyl, acetyl, benzoyl, tert-butoxycarbonyl (Boc), para-methoxybenzyloxycarbonyl, isopropoxycarbonyl, phthaloyl, succinyl, benzyl, diphenylmethyl, triphenylmethyl (trityl), methanesulfonyl, para-toluenesulfonyl, trimethylsilyl, triethylsilyl, triphenylsilyl, and the like. Preferred nitrogen protecting groups of the instant invention are benzyloxycarbonyl (Cbz) and tert-butoxycarbonyl (Boc).

The term "aprotic solvent," as used herein, refers to solvents in which the starting materials and products are at least partially soluble and which does not donate protons during reactions in which it is not used as a reagent. Examples of aprotic solvents include, $C_2$–$C_5$ alkylamides such as formamide, N,N-dimethylformamide, N,N-dimethylacetamide, and the like; $C_4$–$C_6$ dialkoxyalkyls such as DME, 1,2-diethoxyethane, and the like; $C_3$–$C_{10}$ ketones such as acetone, 2-butanone; 3-pentanone, 2-butanone, 2-pentanone, 2,5-heptanedione, tert-butyl methyl ether, and the like; optionally substituted $C_1$–$C_7$ hydrocarbons such as pentane, hexane, heptane, nitromethane, acetonitrile, and the like; optionally substituted aromatic hydrocarbons such as benzene, toluene, 1,4-dichlorobenzene, nitrobenzene, and the like; ethers such as diethyl ether, diisopropyl ether, and the like; and esters such as ethyl acetate isopropyl acetate, and the like.

The term "azido," as used herein, refers to —$N_3$.

The term "carbonyl," as used herein, refers to —C(O)—.

The term "carboxamido," as used herein, refers to an amide; for example, an amino group, as defined herein, attached to the parent molecular group through a carbonyl group, as defined herein.

The term "carboxyl," as used herein, refers to —$CO_2H$ or a derivative formed by replacement of the hydrogen atom thereof by a carboxyl protecting group.

The term "carboxyl protecting group," as used herein, refers to selectively introducible and removable groups which protect carboxyl groups against undesirable side reactions during synthetic procedures and includes all conventional carboxyl protecting groups. Examples of carboxyl groups include methyl, ethyl, n-propyl, isopropyl, 1,1-dimethylpropyl, n-butyl, tert-butyl, phenyl, naphthyl, benzyl, diphenylmethyl, triphenylmethyl (trityl), para-nitrobenzyl, para-methoxybenzyl, acetylmethyl, benzoylmethyl, para-nitrobenzoylmethyl, para-bromobenzoylmethyl, 2-tetrahydropyranyl 2-tetrahydrofuranyl, 2,2,2-trichloroethyl cyclopropyl, cyclobutyl, cyclopentyl, cyclohexyl, methoxymethyl, methoxyethoxymethyl, arylalkoxyalkyl benzyloxymethyl 1,1-dimethyl-2-propenyl, 3-methyl-3-butenyl, allyl, and the like. Preferred carboxyl protecting groups of the instant invention are alkyl and arylalkyl.

The term "cyano," as used herein, refers to —CN.

The term "cycloalkyl," as used herein, refers to a monovalent saturated cyclic hydrocarbon group having from three to seven carbons.

The term "cycloalkylalkyl," as used herein, refers to a cycloalkyl group, as defined herein, attached to the parent molecular group through an alkyl group, as defined herein.

The terms "first acid" and "second acid," as used herein, refer to reagents capable of donating protons during the course of a chemical reaction. Examples of acids include mineral acids such as hydrochloric, hydrobromic, hydroiodic, sulfuric, phosphoric, and the like; organic acids such as formic, acetic, propionic, trifluoroacetic, and the like; and sulfonic acids such as methanesulfonic, para-toluenesulfonic, para-bromosulfonic, para-nitrosulfonic, and the like. The acid chosen for a particular conversion depends on the nature of the starting materials, the solvent or solvents in which the reaction is conducted, and the temperature at which the reaction is conducted.

The terms "first base" and "second base," as used herein, refer to reagents capable of accepting protons during the course of a chemical reaction. Examples of first and second bases include carbonates such as lithium carbonate, lithium bicarbonate, sodium carbonate, sodium bicarbonate, potassium carbonate, potassium bicarbonate, cesium carbonate, and the like; phosphates such as potassium phosphate, potassium hydrogen phosphate, potassium dihydrogen phosphate, and the like; trialkylamines such as triethylamine, diisopropylethylamine, and the like; heterocyclic amines such as imidazole, pyridine, pyridazine, pyrimidine, pyrazine, and the like; anionic nitrogen bases such as lithium bis(trimethylsilylamide), sodium bis (trimethylsilylamide), potassium bis(trimethylsilylamide), lithium diisopropylamide (LDA), and the like; and bicyclic amines such as DBN, DBU, and the like. The base chosen for a particular conversion depends on the nature of the starting materials, the solvent or solvents in which the reaction is conducted, and the temperature at which the reaction is conducted.

The term "halo," as used herein refers to F, Cl, Br, or I.

The term "heteroaryl," as used herein, refers to cyclic, aromatic five- and six-membered groups, wherein at least one atom is selected from the group consisting of nitrogen, oxygen, and sulfur, and the remaining atoms are carbon. The five-membered rings have two double bonds, and the six-membered rings have three double bonds. Heteroaryls of the instant invention are exemplified by fliranyl, thienyl, pyrrolyl, oxazolyl, thiazolyl, imidazolyl, isoxazolyl, isothiazolyl, oxadiazolyl, oxadiazolyl, triazolyl, thiadiazolyl, pyridyl, pyridazinyl, pyrimidinyl, pyrazinyl, pyrazolyl, triazinyl, and the like. The heteroaryl groups of the instant invention are connected to the parent molecular group through a carbon atom in the heteroaryl ring. The heteroaryl groups of the instant invention can be optionally substituted with one, two, or three radicals independently selected from the group consisting of alkyl, alkenyl, alkynyl, alkoxy, alkanoyl, alkanoyloxy, alkoxycarbonyl, alkylsulfonyl, amino, aminosulfonyl, azido, carboxamido, carboxy, cyano, halo, hydroxyl, nitro, perfluoroalkyl, perfluoroalkoxy, thioalkoxy, phenyl, and a second heteroaryl group selected from the group consisting of furanyl, thienyl, pyrrolyl, oxazolyl, thiazolyl, imidazolyl, isoxazolyl, isothiazolyl, oxadiazolyl, oxadiazolyl, triazolyl, thiadiazolyl, pyridyl, pyridazinyl, pyrimidinyl, pyrazinyl, pyrazolyl, and triazinyl. The phenyl and heteroaryl groups substituting the heteroaryl groups of the instant invention are attached to the parent heteroaryl group through either a covalent bond, an alkyl group, an oxygen, or a carbonyl group. The phenyl and heteroaryl groups attached to the parent heteroaryl groups of the instant invention can also be further substituted with one, two, or three substituents independently selected from the group consisting of alkyl, alkoxy, carboxyl, azido, carboxaldehyde, halo, hydroxyl, perfluoroalkyl, and perfluoroalkoxy. The heteroaryl groups of the instant invention can also be fused to a phenyl ring, in which case the heteroaryl group can be connected to the parent molecular group through either the heteroaryl part or the phenyl part of the fused ring system. Heteroaryl groups of this type are exemplified by quinolinyl, isoquinolinyl, benzofuranyl, indolyl, and the like.

The term "hydroxyl," as used herein, refers to —OH or a derivative formed by replacement of the hydrogen atom thereof with a hydroxyl protecting group.

The term "hydroxyl protecting group," as used herein, refers to selectively introducible and removable groups which protect hydroxyl groups against undesirable side reactions during synthetic procedures. Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, tert-butyl, 2,2,2-trichloroethyl, 2-trimethylsilylethyl, 1,1-dimethyl-2-propenyl, 3-methyl-3-butenyl, allyl, benzyl, para-methoxybenzyldiphenylmethyl, triphenylmethyl (trityl), tetrahydrofuryl methoxymethyl, methylthiomethyl, benzyloxymeihyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the instant invention are acetyl (Ac or —C(O)CH$_3$), benzoyl (Bn or —C(O)C$_6$H$_5$), and trimethylsilyl (TMS or —Si(CH$_3$)$_3$).

The tero "oxidizing agent," as used herein, refers to reagents useful for oxidizing the 3-hydroxyl of the macrolide ring to the 3-carbonyl. Preferred oxidizing agents are N-chlorosuccinimide-dimethyl sulfide (Corey-Kim) or carbodiimide-DMSO (modified Swern).

The term "palladium catalyst," as used herein, refers to optionally supported palladium(0) such as palladium metal, palladium on carbon, palladium on acidic, basic, or neutral alumina, and the like; palladium(0) complexes such as tetrakis(triphenylphosphine)palladium(0); palladium(II) salts such as palladium acetate or palladium chloride; and palladium(II) complexes such as allylpalladium(II) chloride dimer, (1,1'-bis(diphenylphosphino)ferrocene)-dichloropalladium(II), bis(acetato)bis(triphenylphosphine)palladium(II), and bis(acetonitrile)dichloropalladium(II).

The term "perfluoroalkoxy," as used herein, refers to a perfluoroalkyl group attached to the parent group through an oxygen atom.

The term "perfluoroalkyl," as used herein, refers to an alkyl group in which all of the hydrogen atoms have been replaced with fluoride atoms.

The term "pharmaceutically acceptable salt," as used herein, refers to salts or zwitterionic forms of the compounds of the instant invention which are water or oil-soluble or dispersible, which are suitable for treatment of diseases without undue toxicity, irritation, and allergic response, which are commensurate with a reasonable benefit/risk ratio, and which are effective for their intended use. The salts can be prepared during the final isolation and purification of the compounds or separately by reacting an amino group with a suitable acid. Representative acid addition salts include acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylpropionate, picrate, pivalate, propionate, succinate, tartrate, thiocyanate, trichloroacetic, trifluoroacetic, phosphate, glutamate, bicarbonate, para-toluenesulfonate, and undecanoate. Also, amino groups in the compounds of the instant invantion can be quaternized with as methyl, ethyl, propyl, and butyl chlorides, bromides and iodides; dimethyl, diethyl, dibutyl, and diamyl sulfates; decyl, lauryl, myristyl, and stearyl chlorides, bromides, and iodides; benzyl and phenethyl bromides. Examples of acids which can be employed to form pharmaceutically acceptable acid addition salts include inorganic acids such as hydrochloric, hydrobromic, sulphuric, and phosphoric and organic acids such as oxalic, maleic, succinic, and citric.

Basic addition salts can be prepared during the final isolation and purification of the compounds by reacting a carboxyl group with a suitable base such as the hydroxide, carbonate, or bicarbonate of a metal cation or with ammonia or an organic primary, secondary or tertiary amine. Pharmaceutically acceptable salts cations based on lithium, sodium, potassium, calcium, magnesium, and aluminum and nontoxic quaternary ammonia and amine cations such as ammonium, tetramethylammonium, tetraethylammonium, methylamine, dimethylamine, trimethylamine, triethylamine, diethylamine, ethylamine, tributlyamine, pyridine, N,N-dimethylaniline, N-methylpiperidine, N-methylmorpholine, dicyclohexylamine, procaine, dibenzylamine, N,N-dibernzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The term "phenyl," as used herein, refers to a six-membered, aromatic, carbocyclic group. The phenyl groups of the instant invention can be optionally substituted by one, two, three, four, or five radicals independently selected from the group consisting of alkyl, alkenyl, alkynyl, alkoxy, alkanoyl, alkanoyloxy, alkoxycarbonyl, alkylsulfonyl, amino, aminosulfonyl, azido, carboxamido, carboxy, cyano, halo, hydroxyl, nitro, perfluoroalkyl, perfluoroalkoxy, thioalkoxy, another phenyl group, and a heteroaryl selected from the group consisting of furanyl, thienyl, pyrrolyl, oxazolyl, thiazolyl, imidazolyl, isoxazolyl, isothiazolyl, oxadiazolyl, oxadiazolyl, triazolyl, thiadiazolyl, pyridyl, pyridazinyl, pyrimidinyl, pyrazinyl, and triazinyl. The phenyl group and the heteroaryl groups which are attached to the parent phenyl group are attached through either a covalent bond, an alkyl group, an oxygen atom, or a carbonyl group. The phenyl and heteroaryl groups optionally substituting the parent phenyl groups of the instant invention can also be further substituted with one, two, or three substituents independently selected from the group consisting of alkyl, alkoxy, carboxyl, azido, carboxaldehyde, halo, hydroxyl, perfluoroalkyl, and perfluoroalkoxy.

The term "phenylalkyl," as used herein, refers to an phenyl group, as defined herein, attached to the parent molecular group through an alkyl group, as defined herein.

The term "phenylsulfonyl," as used herein, refers to a phenyl group, as defined herein, attached to the parent molecular group through a sulfonyl, as defined herein.

The term "sulfonyl," as used herein, refers to —$SO_2$—.

The terms "treated" or "treatment," as used below, refer to contacting, mixing, diluting, or reacting one or more chemical entities by a reasonable and usual manner in which chemicals are combined. Normal concentrations (0.01M to 10M, typically 0.1M to 1M), temperatures (−10° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive reactions) are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Numerous asymmetric centers exist in the compounds of the instant invention. The instant invention contemplates stereoisomers and mixtures thereof. Individual stereoisomers of compounds are prepared by synthesis from starting materials containing the chiral centers. These starting materials are either commercially available or are made by the methods described hereinbelow and resolved by techniques well-known in the art.

Percentages obtained by HPLC analyses of starting materials and products were calculated from the the area under the curve (AUC).

All of the processes of this invention can be conducted as continuous processes. The term "continuous process," as used herein, refers to the conduction of a reaction to provide an intermediate followed by use, optionally in situ, of the intermediate, without isolation, in a subsequent reaction. The term "in situ," as used herein, refers to use of an intermediate in the solvent or solvents in which the intermediate was prepared without removal of the solvent.

The instant invention will be better understood in connection with Schemes 1–8. It will be readily apparent to one of ordinary skill in the art that the process of the instant invention can be practiced by substitution of the appropriate reactants and that the order of the steps themselves can be varied.

Erythromycins can be protected as 9-oximes as described in U.S. Pat. Nos. 4,990,602; 4,990,602; 4,331,803; 4,680, 386; and 4,670,549. Preferred oximes are those wherein R and R together are O-(1-isopropoxycyclohexylketal)oxime. Reaction of erythromycin A with hydroxylamine and formic acid in methanol provides an erythromycin A 9-oxime derivative which can be further derivatized without isolation. The preferred amount of hydroxylamine is about 7 to about 10 molar equivalents per molar equivalent of erythromycin A. From about 2 to about 5 molar equivalents of formic acid are used for each molear equivalent of erythromycin A.

Erythromycins can also be protected as C-9 hydrazones (as described in U.S. Pat. No. 5,929,219) by applying chemistry described in *J. Am. Chem. Soc.*, 78, 388–395, (1956). The erythromycin C-9 hydrazones are prepared by reacting the erythromycin with an optionally substituted hydrazine in an alcohol for about 12 to about 36 hours. The C-9 hydrazone erythromycin can further be reacted with nitrogen protecting group precursors by the methods described in "Protective Groups in Organic Synthesis", 3rd edition, John Wiley & Sons, New York, Chapter 7, (1999). For example, the nitrogen of the C-9 hydrazone erythromycin can be protected by treatment of the former with a silylating agent such as triisopropylsilyl triflate and a base base such as triethylamine in a solvent such as dichloroethane to provide 9-(N-triisopropylsilyl)hydrazone erythromycin derivatives.

Erythromycin 9-hydrazones can be converted to an azines by methods described in U.S. Pat. No. 3,780,020 and German Patent 1,966,310. For example, the hydrazone can be treated with the appropriate ketone, aldehyde or orthoformate, optionally with a cosolvent, and optionally with a dehydrating agent such as molecular sieves. The reaction is conducted at a temperature between room temperature and the boiling point of the ketone, aldehyde, or co-solvent for about 1 to about 24 hours. The azine nitrogen can be further protected by treatment with the appropriate ketal in the presence of catalytic formic or acetic acid at ambient temperature for about 18 hours.

The 2'- and 4"-hydroxyl groups of each of the aformentioned erythromycin derivatives can be protected sequentially or simultaneously by reaction with a suitable hydroxyl protecting group precursor in an aprotic solvent as described in U.S. Pat. No. 5,892,008. Typical hydroxyl-protecting reagents include acetylating agents and silylating agents such as acetyl chloride, acetic anhydride, benzoyl chloride, benzoic anhydride, benzyl chloroformate, hexamethyldisilazane, and trialkylsilyl chlorides. For the unisolated erythromycin A 9-oxime described above, it is preferred that the benzoylation is carried out with benzoic anhydride, optionally with base, in THF, optionally with isopropyl acetate, to provide the protected erythromycin A 9-oxime. For the other erythromycin derivatives described above, benzoylation of the hydroxyl group is typically accomplished by treatment of the erythromycin 9-oxime derivative with a benzoylating reagent such as benzoic anhydride.

Once protected, the erythromycin derivatives can be further derivatized by the chemistry described below.

Scheme 1

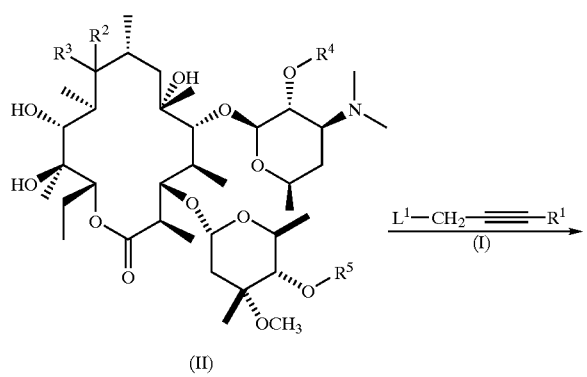

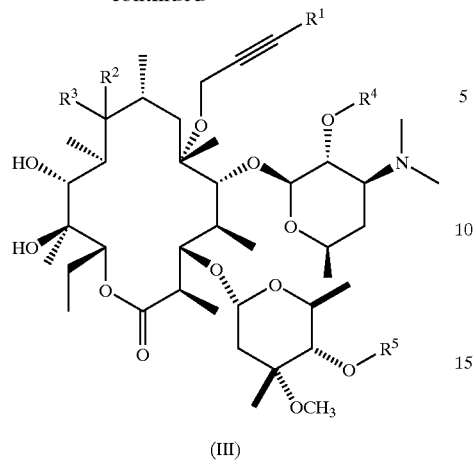

(III)

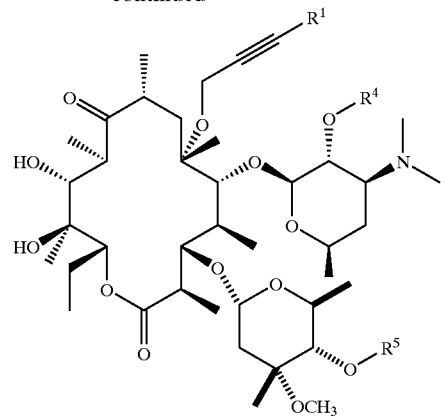

(IV)

As shown in Scheme 1, conversion of compounds of formula (II) to compounds of formula (III) by simultaneous treatment of the former over about 3 to about 3.5 hours with optionally substituted propargyl chlorides, bromides, iodides, triflates, or sulfonates in the presence of a base such as lithium methoxide, lithium ethoxide, lithium isopropoxide, lithium tert-butoxide sodium methoxide, sodium ethoxide, sodium isopropoxide, sodium tert-butoxide, potassium methoxide, potassium ethoxide, potassium isopropoxide, and potassium tert-butoxide, preferably potassium tert-butoxide. Preferred solvents used for this conversion are aprotic solvents such as DMSO, diethylsulfoxide, N,N-dimethylformamide, N,N-dimethylacetamide, N-methyl-2-pyrrolidone, mixtures thereof, or mixtures of one of these solvents with ether, tetrahydrofuran, 1,2-dimethxyethane, or acetonitrile. In a preferred embodiment, the solvent used for this conversion is a mixture of DMSO and THF. The reaction is preferably conducted at about 0° C. to about 5° C. for about 3 to about 3.5 hours.

As shown in Scheme 2, conversion of compounds of formula (III) to compounds of formula (IV) can be accomplished by treatment of the former with nitrous acid formed in situ by the reaction of sodium nitrite with acids such as HCl, $H_2SO_4$, or TFA at pressures between about 15 psi to about 70 psi in solvents comprising a mixture of water and an alcohol such as methanol, ethanol, propanol, isopropanol, or tert-butanol, preferably ethanol. The deoximation is preferably accomplished with hydrochloric acid present in about 5 to about 10 molar equivalents (preferably about 8) per molar equivalent of the compound of formula (III) and the sodium nitrite present in about 5 to about 8 molar equivalents (preferably 7.5) per molar equivalent of the compound of formula (III). The reaction is preferably conducted at about 20° C. to about 40° C. for about 2.5 hours to about 16 hours. The pressure of the reaction can be attained by in situ formation of nitrous acid from the reaction of sodium nitrite with acid, or alternatively introduction of $N_2O_4$ directly into the system.

Scheme 2

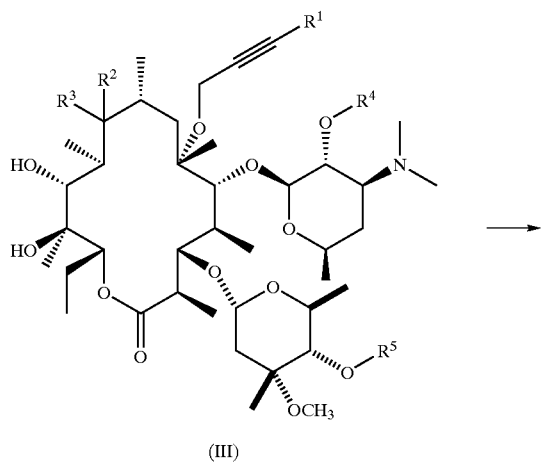

(III)

Scheme 3

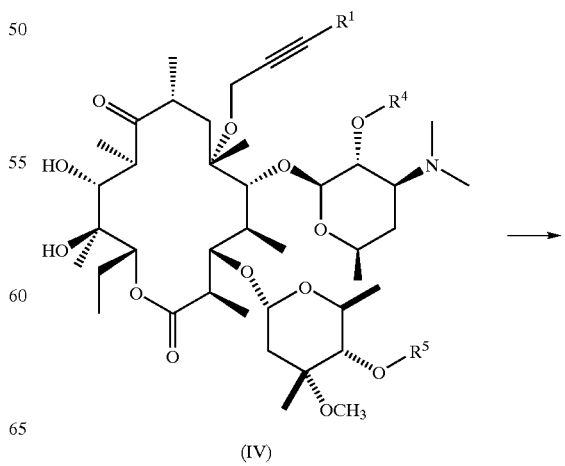

(IV)

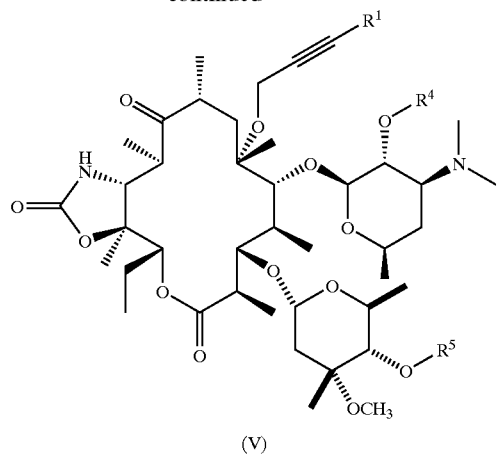

(V)

As shown in Scheme 3, conversion of compounds of formula (IV) to compounds of formula (V) can be accomplished by (a) treatment of the former with an excess of base such as sodium hydride, sodium bis(trimethylsilyl)amide, DBU, imidazole, and the like, in the presence of carbonyldiimidazole followed by (b) treatment of the intermediate formed in step (a) with ammonia or ammonium hydroxide in the presence of a base such as potassium tert-butoxide. Step (a) is typically conducted in a mixture of DMF and THF for about 8 to about 24 hours at temperatures between about −30° C. to about room temperature. Step (b) is typically conducted in THF at temperatures of about 0° C. to about 20° C. Portions of this reaction sequence follow procedures described in *J. Org. Chem.*, 1988, 53, 2340.

Scheme 4

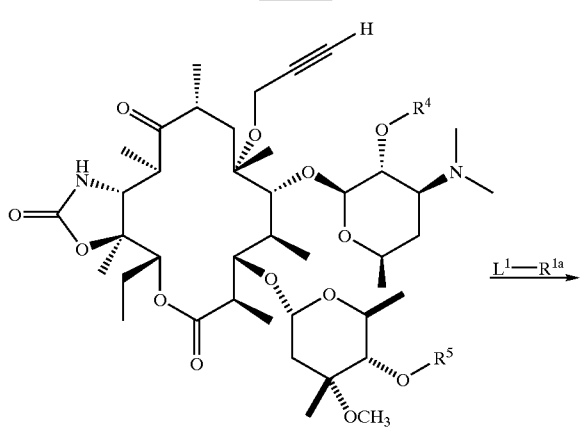

(V-a)

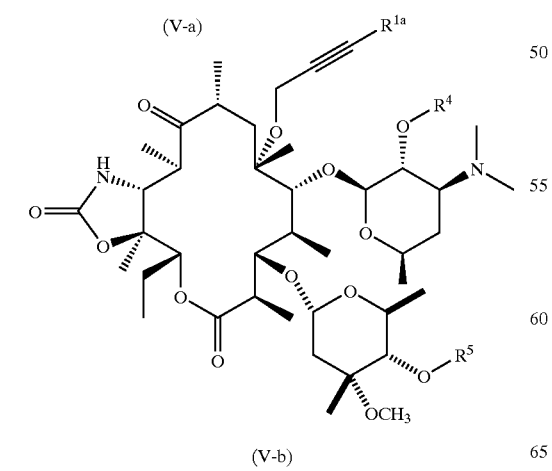

(V-b)

As shown in Scheme 4, compounds of formula (V-a) can be converted to compounds of formula (V-b) by treatment of the former with compounds of formula $L^1$—$R^{1a}$, a palladium catalyst, an additive and a first base. $L^1$ represents any number of covalent bond precursors such as halides (preferably bromide or iodide), trifluoromethanesulfonate, and sulfonate, and $R^{1a}$ represents optionally substituted heteroaryl. Examples of palladium catalysts include optionally supported palladium(0), palladium(0) complexes, palladium(II) salts, and palladium(II) complexes (preferably palladium(II) acetate); examples of additives include monodentate phosphorus-containing ligands and bidentate phosphines (preferably triphenylphosphine); and examples of bases include trialkylamines, heterocyclic amines, and bicyclic amines (preferably triethylamine). The coupling reactions are conducted in aprotic solvents such as DMF, DMSO, DME, acetonitrile THF, or mixtures thereof at temperatures from about room temperature to about 150° C., depending on the coupling method chosen and the nature of $L^1$. A thorough survey of coupling procedures, reagents, and solvents for transition metal-catalyzed couplings is provided in "Comprehensive Organic Transformations. A Guide to Functional Group Preparations," VCH Publishers, New York (1989), and references therein.

Scheme 5

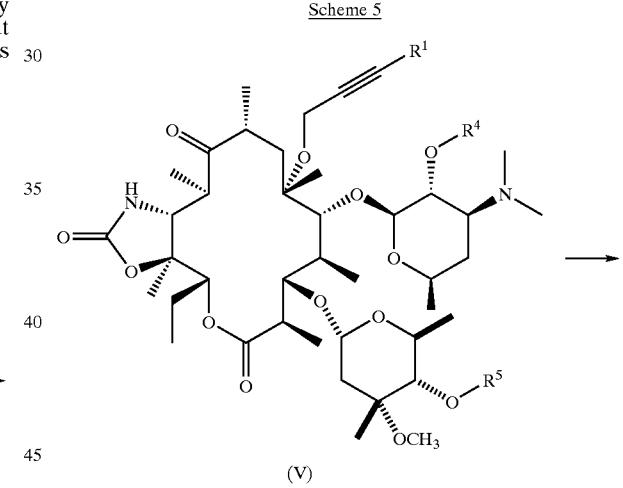

(V)

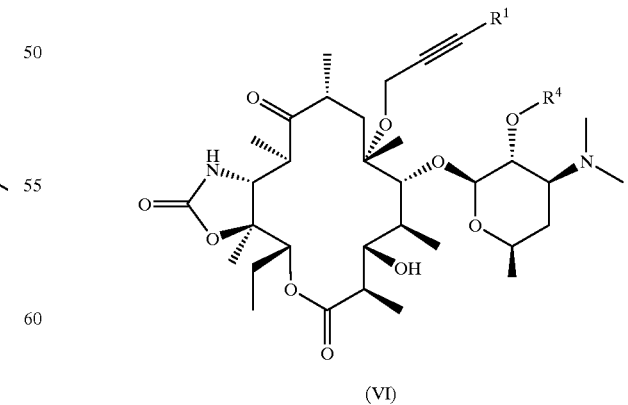

(VI)

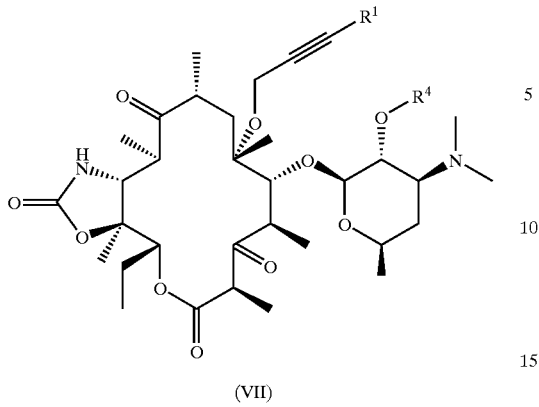

(VII)

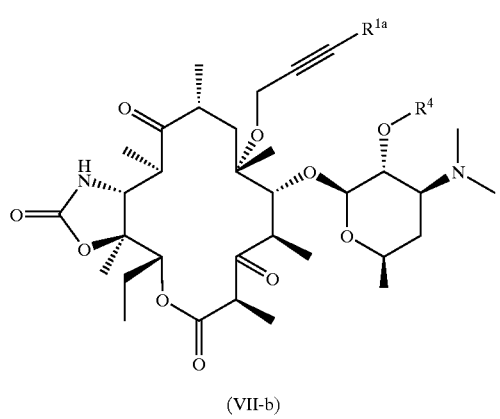

(VII-b)

As shown in Scheme 5, compounds of formula (V) can be converted to compounds of formula (VI) by treatment of the former with mild aqueous acid or by enzymatic hydrolysis to remove the cladinose moiety from the 3-hydroxy group. Representative acids include dilute hydrochloric acid, sulfuric acid, acetic acid, chloroacetic acid, dichloroacetic acid, or trifluoroacetic acid. Suitable solvents for the reaction include methanol, ethanol, isopropanol, butanol, acetone, and mixtures thereof. Reaction times are typically about 0.5 to about 24 hours. The preferred reaction temperature is about 5° C. to about 60° C., depending on the method chosen.

The conversion of compounds of formula (VI) to compounds of formula (VII) can be accomplished by treatment of the former with an N-chlorosuccinimide-dimethyl sulfide complex (Corey-Kim) or a carbodiimide-DMSO complex (modified Swern). In a preferred method, the reactions are conducted in a chlorinated solvent such as dichloromethane or chloroform at about −10° C. to about 25° C.

As shown in Scheme 6, conversion of compounds of formula (VII-a) to compounds of formula (VII-b) can be achieved by treatment of the former with the reagents and under the conditions described for the conversion of compounds of formula (V-a) to compounds of formula (V-b) as described in Scheme 4.

Scheme 7

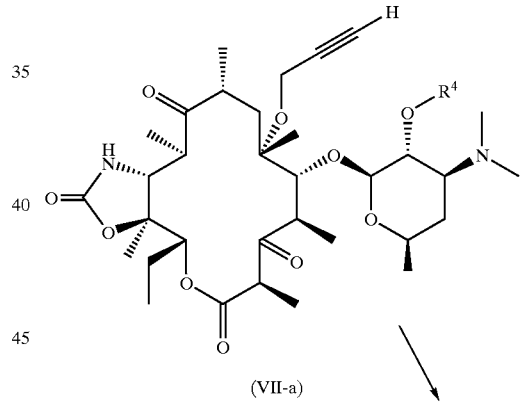

(VII-a)

Scheme 6

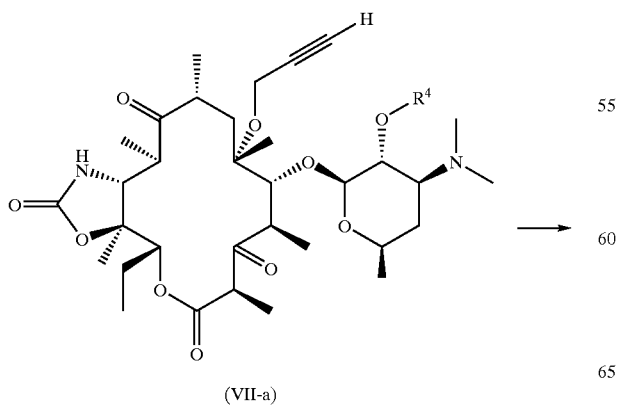

(VII-a)

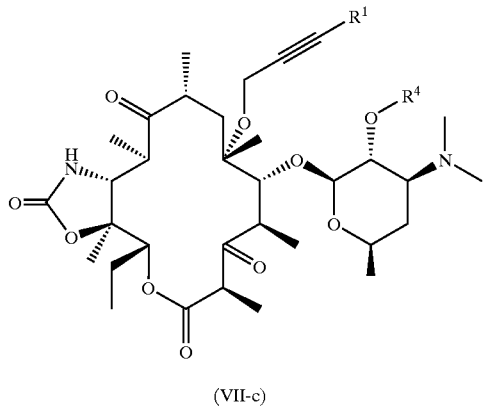

(VII-c)

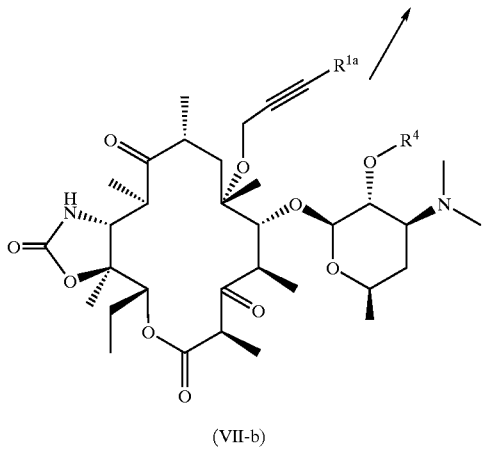

(VII-b)

As shown in Scheme 7, removal of the protecting groups on the cladinose groups of compounds of formulas (VII-a) and (VII-b) to provide compounds of formula (VII-c) can be achieved by treatment of the former with methanol at temperatures between 0° C. and reflux. Reaction times are typically about 0.5 to about 24 hours, depending on the temperature.

Scheme 8

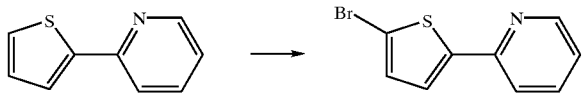

The preparation of a particularly preferred embodiment of the compound of formula $L^1$—$R^{1a}$ a is shown in Scheme 8. Bromination of 2-(2-thienyl)pyridine to provide 2-(5-bromo-2-thienyl)pyridine can be achieved by treatment of the former with bromine or N-bromosuccinimide (preferably the latter) in the presence of a catalyst such as hydrobromic or methanesulfonic acid in a solvent such as acetic acid, dichloromethane, chloroform, tert-butyl methyl ether, or mixtures thereof (preferably tert-butyl methyl ether). The reaction is typically conducted between 20° C. and 50° C., and the reaction times are typically about 0.5 to about 24 hours.

The instant invention will now be described in connection with certain particularly preferred embodiments of the chemistry discussed above. These examples are not intended to limit its scope. On the contrary, the invention covers all alternatives, modifications, and equivalents which are included within the scope of the claims. Thus, the following examples will illustrate an especially preferred practice of the invention, it being understood that the examples are for the purposes of illustration of certain preferred embodiments and are presented to provide what is believed to be the most useful and readily understood description of its procedures and conceptual aspects.

Unless otherwise noted, all reagents were obtained from commercial suppliers and were used without further purification. All reactions except the deoximation were carried out under an atmosphere of nitrogen. $^1$H NMR spectra were obtained on a General Electric QE-300 NMR instrument at 300 MHz. Chemical shifts are expressed in ppm downfield from internal tetramethylsilane. $^1$H NMR data are tabulated in the following order: chemical shift, multiplicity (s, singlet: d, doublet: t, triplet; q, quartet; m, multiplet), number of protons, and coupling constant(s) in hertz (Hz). Mass spectra were recorded with a Finnagan LCQ mass spectrometer. All new compounds were characterized by full spectroscopic and analytical data. Yields refer to spectroscopically homogenous materials. Microanalyses were performed by the Abbott Analytical Department.

EXAMPLE 1

Compound of Formula (II): $R^2$ and $R^3$ Together are =N—O—C($R^{7a}$)($R^{7b}$)—OR $R^4$ and $R^5$ are Hydrogen; $R^{7a}$ ad $R^{7b}$ Together are Pentylene; $R^8$ is Isopropyl A stirred solution of a compound of formula (II) (wherein $R^2$ and $R^3$ together are =N—O—C($R^{7a}$)($R^7$b)—OR$^8$, $R^4$ and $R^5$ are —Si(CH$_3$)$_3$, $R^{7a}$ and $R^{7b}$ together are pentylene, and $R^8$ is isopropyl) (250 g) in THF (250 mL) at room temperature was treated in one portion with 1M TBAF in THF (508 mL), stirred at room temperature for 5 hours, treated with ethyl acetate (2.25 L), washed sequentially with water (750 mL) and 5% NaCl (750 mL) at 45° C., concentrated to about 400 mL, treated with ethyl acetate (1.25 L), and concentrated to about 400 mL. This procedure was repeated, and the resulting solution was treated with enough ethyl acetate to provide a final volume of 1.5 L. The yield of the desired product was quantitative. A pure sample was isolated for analysis. MS m/z 889 (M+H)$^+$; $^1$H NMR (300 MHz, CDCl$_3$) δ 5.12 (m, 1H), 4.92 (m, 1H), 4.50 (s, 1H), 4.45 (d, J=7 Hz, 1H), 4.15–4.0 (m, 2H), 3.80–3.70 (m, 1H), 3.70 (s, 1H), 3.59 (d, J=8 Hz, 1H), 3.55–3.45 (m, 1H), 3.41 (br s, 1H), 3.32 (s, 3H), 3.26–3.15 (m, 2H), 3.1–3.0 (m, 1H), 2.94–2.85 (m, 1H), 2.75 (q, J=7 Hz, 1H), 2.50–2.35 (m, 2H), 2.29 (s, 6H), 2.05–1.76 (m, 5H), 1.70–1.35 (m, 18H), 1.42 (s, 3H), 1.32 (d, J=7 Hz, 2H), 1.04 (d, J=7 Hz, 4H), 0.82 (t, J=7 Hz, 3H); Anal. calcd for C$_{46}$H$_{84}$N$_2$O$_{14}$: C, 62.14; H, 9.52; N, 3.15. Found: C, 61.96; H, 9.78; N, 3.02.

EXAMPLE 2

Compound of Formula (II): $R^2$ and $R^3$ are =N—O—C($R^{7a}$)($R^{7b}$)—OR$^8$; $R^4$ and $R^5$ are —C(O)C$_6$H$_5$; $R^{7a}$ and $R^{7b}$ Together are Pentylene; $R^8$ is Isopropyl A mixture of benzoic anhydride (164.2 g) and 4-dimethylaminopyridine (29.6 g) at room temperature was treated with the solution of Example 1 and triethylamine (49.0 g), stirred at room temperature for 24 hours, treated with 5% NaHCO$_3$ (1.5 L), and stirred vigorously for 1 hour. The organic layer was separated, washed sequentially with 5% NaHCO$_3$ (1.5 L), 5% KH$_2$PO$_4$ (2×1.5 L) and water (1.5 L), filtered, concentrated to about 400 mL, treated with heptane (1.25 L), concentrated to about 400 mL, treated again with heptane (1.25 L), and concentrated to about 1 L. The resulting slurry was heated to reflux for about 30 minutes to dissolve the solids, cooled to 0–5° C., and stirred for another 2 hours to provide crystals. The crystals were filtered, washed with heptane (500 mL), and dried under vacuum at 50° C. to provide 225.6 g (87%) of the desired product. MS m/z 1097 (M+H)$^+$; $^1$H NMR (300 MHz, CDCl$_3$) δ 8.04 (dd, J=7 Hz, 4H), 7.59 (m, 2H), 7.46 (m, 4H), 5.12 (m, 1H), 4.92 (m, 1H), 4.50 (s, 1H), 4.45 (d, J=7 Hz, 1H), 4.15–4.0 (m, 2H), 3.80–3.70 (m, 1H), 3.70 (s, 1H), 3.59 (d, J=8 Hz, 1H), 3.55–3.45 (m, 1H), 3.41 (br s, 1H), 3.32 (s, 3H), 3.26–3.15 (m, 2H), 3.1–3.0 (m, 1H), 2.94–2.85 (m, 1H), 2.75 (q, J=7 Hz, 1H), 2.50–2.35 (m, 2H), 2.29 (s, 6H), 2.05–1.76 (m, 5H), 1.70–1.35 (m, 18H), 1.42 (s, 3H), 1.32 (d, J=7 Hz, 2H), 1.27–1.07 (m, 22H), 1.04 (d, J=7 Hz, 4H), 0.82 (t, J=7 Hz, 3H); Anal. calcd for $C_{60}H_{92}N_2O_{16}$: C, 65.67; H, 8.45; N, 2.55. Found: C, 65.43; H, 8.66; N, 2.33.

EXAMPLE 3

Compound of Formula (III-b): $R^4$ and $R^5$ are —C(O)$C_6H_5$

A 200-gallon reactor was charged with Example 2 (21.9 kg), THF (77 kg) and DMSO (95 kg). The mixture was agitated while cooling to an internal temperature of 0° C. to 2° C. 3-Bromo-1-propyne (propargyl bromide) (11.0 kg) and potassium tert-butoxide (26.0 kg) were diluted with THF (128.0 kg) in pressure canisters and placed atop a weigh balance. The reagents were then simultaneously charged to the reactor at a predetermined rate over 3 hours with the addition controlled by nitrogen pressure on the canisters. The reaction was complete when the amount of Example 2 was less than 5%. The reaction mixture was cooled to below 10° C. and treated sequentially at this temperature with tert-butyl methyl ether (280 kg), triethylamine (18.0 kg) and chilled water (280 kg) with minimal agitation to avoid emulsion formation. The aqueous layer was removed from the reaction mixture, and the remainder was treated with 3% NaCl. The layers were separated, and the organic layer was weighed and assayed before being concentrated under vacuum at a bath temperature of not more than 45° C. The organic layer was then concentrated to about 70 L and solvent exchanged with acetonitrile (300 kg), which caused the product to precipitate. The suspension was concentrated to about 130 L, cooled to 10° C., and filtered. The reactor was rinsed with fresh acetonitrile (15 kg), and the rinse was used as a wash for the wetcake. The wetcake was dried on the filter for no longer than 6 hours and dried in a vacuum oven with a nitrogen purge at 45° C. to provide 18.2 kg (78%) of the desired product. MS m/z 1135 (M+H)$^+$; $^1$H NMR (300 MHz, CDCl$_3$) δ 8.15 (br d, J=10.7, 3.7 Hz, 4H), 7.68 (br dd, J=16.2, 13.6 Hz, 2H), 7.55 (q, J=14.3, 6.6 Hz, 4H), 5.16 (dd, J=11.8, 10.3 Hz, 2H), 5.06 (dd, J=12.5, 10.3 Hz, 2H), 4.60 (m, 1H), 4.45 (br s, 1H), 4.10 (m, 4H), 3.80 (m, 3H), 3.65 (s, OCH$_3$, 3H), 3.34 (br s, 1H), 3.05 (m, 1H), 2.91 (m, 1H), 2.68 (br q, J=13.6 Hz, 1H), 2.60 (d, J=15.0 Hz, 1H), 2.49 (t, J=2.2 Hz, 1H), 2.45 (br s, N(CH$_3$)$_2$, 6H), 2.15–1.75 (m, 10H), 1.70–1.38 (m, 15H), 1.37–1.05 (m, 16H), 0.9 (t, J=7.4 Hz, 3H), 0.85 (d, J=7.7 Hz, 3H); Anal. calcd for $C_{63}H_{94}N_2O_{16}$: C, 66.67; H, 8.29; N, 2.47. Found: C, 66.48; H, 8.37; N, 2.39.

EXAMPLE 4

Compound of Formula (IV-a): $R^4$ and $R^5$ are —C(O)$C_6H_5$

A first pressure reactor was pressure checked at 40 psi then charged sequentially with Example 3 (8.0 kg) and ethanol (32.0 kg). The slurry was stirred at room temperature, treated with 2M HCl (28.2 L), and stirred for 15 minutes. The first pressure reactor containing the slurry was then sealed. A second pressure reactor was charged with sodium nitrite (3.65 kg) and water (23 kg). This solution was added under positive nitrogen pressure to the slurry in the first pressure reactor. The reaction in the first pressure reactor proceeded for 3 hours at 35–40° C. at an initial pressure of about 30 psi and a final pressure of about 50 psi. The reaction was sampled using the internal pressure, and the pressure was released. The reactor was sealed again, and the reaction was continued for 1 hour, during which the pressure increased about 10–15 psi. The reaction sample was initially gummy but solidified at room temperature. The pressure was released and the internal temperature was cooled to 25° C. The mixture was stirred for 1 hour and filtered. The wetcake was washed with water (10 kg) and dried in a vacuum oven at 65° C. to provide 6.0 kg of the nitrate salt of the desired product as a tan powder in 75% yield. This product was combined with the product from another run.

A mixture of the combined nitrate salts (16.9 kg), tert-butyl methyl ether (124 kg), and cyclohexane (132 kg) was heated to 65° C., stirred for 30 minutes, cooled to 0° C., stirred for 2 hours, and filtered. The wetcake washed with cold 1:1 tert-butyl methyl ether:cyclohexane (55 kg), blown dry over 18 hours, charged to a reactor with sequential distilled water (39 kg) and methanol (154 kg) rinsing, and treated with 50% (w/w) K$_2$CO$_3$ (4.6 kg) followed immediately by distilled water (95 kg). The resulting slurry was stirred for at least one hour and filtered. The wetcake was washed with distilled water (102 kg) and dried in a vacuum oven at 65° C. to provide 15.15 kg (71%) of the desired product as a tan powder. MS m/z 980 (M+H)$^+$; $^1$H NMR (300 MHz, CDCl$_3$) δ 8.06–8.03 (m, 4H), 7.64–7.55 (m, 2H), 7.50–7.44 (m, 4H), 5.12–5.05 (m, 3H), 5.01–4.93 (m, 2H), 4.50–4.45 (m, 1H), 4.09–3.98 (dq, J=8, 2.2 Hz, 2H), 3.94–3.87 (m, 2H), 3.78 (d, J=10 Hz, 1H), 3.70–3.67 (m, 2H), 3.56 (s, 3H), 3.16 (br s, 1H), 3.02–2.93 (m, 2H), 2.86–2.80 (m, 1H), 2.66–2.60 (m, 1H), 2.50 (d, J=15 Hz, 1H), 2.44 (t, J=2.2 Hz, 1H), 2.33 (s, 6H), 1.93–1.62 (m, 6H), 1.54 (s, 3H), 149–1.32 (m, 2H), 1.23 (s, 6H), 1.21 (s, 2H), 1.16–1.10 (m, 6H), 1.04 (s, 3H), 0.95 (d, J=6 Hz, 3H), 0.82–0.75 (m, 6H); Anal. calcd for $C_{54}H_{77}NO_{15}$: C, 66.17; H, 7.92; N, 1.43. Found: C, 65.99; H, 8.03; N, 1.32.

EXAMPLE 5

Compound of Formula (V-a): $R^4$ and $R^5$ are —C(O)$C_6H_5$

A 30-gallon reactor was evacuated, purged with nitrogen, and charged sequentially with Example 4 (4.8 kg), 1,1'-carbonyldiimidazole (2.5 kg), THF (18.0 kg) and DMF (6.4 kg). The mixture was agitated, treated with DBU (160 g), stirred at ambient temperature for 1 hour, and heated at 40° C. and for about 18 hours, cooled to –10° C. and treated with liquid ammonia (about 10 kg), stirred for about 1 hour, warmed 15° C., treated with nitrogen gas to remove the ammonia, treated with 1M potassium tert-butoxide in THF (5.2 kg), stirred at ambient temperature for 17 hours, treated with isopropyl acetate (45 kg) and 5% KH$_2$PO$_4$ (25 kg) while slowing the agitation to avoid emulsion formation. The aqueous layer was removed, and the remainder was treated with 5% NaCl (25 kg). The layers are separated, and the organic (upper) layer was weighed and assayed before being concentrated under vacuum at an internal temperature of not more than 45° C. The organic layer was concentrated to about 30 L, treated with additional isopropyl acetate (30 kg), and distilled until a Karl Fisher analysis of the organic extract was less than 1 mg/g. The volume of the extract was kept at about 30 L while being solvent exchanged with isopropyl alcohol (50 kg), during which the product began to crystallize. The suspension was concentrated to about 40 L, cooled to 10° C., and filtered. The reactor was rinsed with cold isopropyl acetate (15 kg), and the rinse was used as a wash for the wetcake. The wetcake was dried on the filter for not less than 2 hours and dried in a vaccum oven with a nitrogen purge at 60° C. to provide 4.44 kg (89%) of the desired product. This product typically contains about 2% of the N-nitroso (from the deoximation step). MS m/z 1005 (M+H)$^+$; $^1$H NMR (300 MHz, CDCl$_3$) δ 8.15 (br m, 4H), 7.6

(br dd, J=7.3, 7.7 Hz, 2H), 7.45 (dt, J=7.7, 1.9 Hz, 4H), 5.78 (br s, 1H), 5.04 (m, 3H), 4.9 (d, J=7.3 Hz, 2H), 4.45 (m, 1H), 4.0 (m, 2H), 3.85 (m, 3H), 3.75 (br s, 1H), 3.67 (br d, J=6.3 Hz, 1H), 3.52 (s, OCH$_3$, 3H), 3.0–2.72 (m, 3H), 2.6–2.43 (m, 3H), 2.33 (s, N(CH$_3$)$_2$, 6H), 1.9–1.6 (m, 10H), 1.48 (br s, 3H), 1.35 (br s, 3H), 1.2 (m, 6H), 1.15 (d, J=6.6 Hz, 3H), 0.95 (d, J=5.9 Hz, 3H), 0.85 (t, J=7.7 Hz, 3H), 0.76 (d, J=7.4 Hz, 3H); Anal. calcd for C$_{55}$H$_{76}$N$_2$O$_{15}$: C, 65.72; H, 7.62; N, 2.79. Found: C, 65.59; H, 7.81; N, 2.48.

EXAMPLE 6

Compound of Formula (VI): R$^1$ is Hydrogen, R$^4$ is —C(O)C$_6$H$_5$

A 5 L, 3-necked round-bottomed flask equipped with a thermocouple, a nitrogen inlet tube and a mechanical stirring apparatus was charged sequentially with Example 5 (268 g), ethanol (1.3 L), and 2M HCl (1.3 L). The mixture was heated at 45° C. for about 12 hours. After cooling to room temperature, the mixture was treated with water (1.3 L) and concentrated to remove the ethanol. The resulting mixture was treated with tert-butyl methyl ether (500 mL), and the resulting layers were agitated and separated. This procedure was repeated twice. The aqueous layer containing the product (bottom) was treated sequentially with isopropyl acetate (2.2 L) and 30% K$_2$CO$_3$ (500 mL) with good mixing. The layers are separated, and the organic layer was removed under vacuum to provide the desired product as a foam which was further dried under high vacuum to provide 200 g (99%) of the desired product as an off-white powder. The desired product was of sufficient purity (96%) to be used directly in the next step. An analytical sample was prepared by crystallization from acetonitrile. MS m/z 743 (M+H)$^+$; $^1$H NMR (300 MHz, CDCl$_3$) δ 8.08 (m, 2H), 7.58 (br dd, J=7.3, 7.7 Hz, 1H), 7.46 (dt, J=7.7, 1.9 Hz, 2H), 5.77 (br s, 1H), 5.04 (m, 3H), 4.78 (d, J=7.3 Hz, 1H), 3.80 (m, 4H), 3.57 (br d, J=6.3 Hz, 2H), 2.99–2.93 (m, 1H), 2.82 (m, 1H), 2.64–2.45 (m, 3H), 2.32 (br s, 6H), 2.00–1.42 (m, 6H), 1.40 (s, 2H), 1.34 (s, 2H), 1.29–1.22 (m, 9H), 1.12 (d, J=6.6 Hz, 3H), 1.07 (d, J=6.6 Hz, 3H), 0.85 (t, J=7.7 Hz, 3H), 0.72 (d, J=7.4 Hz, 3H); Anal. calcd for C$_{40}$H$_{58}$N$_2$O$_{11}$:C, 64.67; H, 7.87; N, 3.77. Found: C, 64.31; H, 7.97; N, 3.45.

EXAMPLE 7

Compound of Formula (VII-a): R$^4$ is —C(O)C$_6$H$_5$

A jacketed flask was charged sequentially with a solution of Example 6 (20.8 g) in THF (150 mL), dimethylsulfide (3.7 g), and diisopropylethylamine (4.7 g). The solution was cooled to about −13° C., treated with a solution of N-chlorosuccinimide (7.1 g, 53.2 mmol) in THF (24 mL) at −11° C. to −13° C., stirred at −15° C.±5° C. for 3 hours, treated sequentially with isopropyl acetate (300 mL) and 0.5M NaOH (120 mL), warmed to room temperature, and stirred for 1 hour. The organic layer was separated, washed with 5% NaCl (2×60 mL) and saturated NaCl (2×60 mL), and concentrated under vacuum to provide an amorphous yellow solid which, when dried under high vacuum, turned into a white foam. The solid was slurried in warm water, filtered, and dried to provide 19.6 g (94%) of the desired product as a white solid after trituration with 10% ethyl acetate/heptane. MS m/z 741 (M+H)$^+$; $^1$H NMR (300 MHz, CDCl$_3$) δ 8.08 (m, 2H), 7.58 (br dd, J=7.3, 7.7 Hz, 1H), 7.46 (dt, J=7.7, 1.9 Hz, 2H), 5.72 (br s, 1H), 5.12–4.94 (m, 3H), 4.59 (d, 7.3 Hz, 1H), 4.35 (d, J=7 Hz, 1H), 3.87 (s, 1H), 3.77–3.55 (m, 4H), 3.07–2.93 (m, 1H), 2.86 (m, 1H), 2.64–2.52 (m, 2H), 2.36 (t, J=3 Hz, 1H), 2.31 (br s, 6H), 2.00–1.86 (m, 2H), 1.62–1.40 (m, 8H), 1.35–1.28 (m, 6H), 1.24 (d, J=6.6 Hz, 3H), 1.17–1.08 (m, 4H), 0.96 (d, J=7 Hz, 3H), 0.85 (t, J=7 Hz, 3H); Anal. calcd for C$_{40}$H$_{56}$N$_2$O$_{11}$: C, 64.85; H, 7.62; N, 3.78. Found: C, 64.68; H, 7.74; N, 3.51.

EXAMPLE 8

Compound of Formula (VII-c): R$^1$ is Hydrogen

A solution of Example 7 (1 g) in methanol (10 mL) was refluxed for 15 hours and concentrated. The concentrate was treated sequentially with tert-butyl methyl ether (10 mL) and 0.5M HCl (10 mL) and stirred for 20 minutes. The aqueous layer was separated and washed with tert-butyl methyl ether (2×10 mL). The HCl layer was diluted with ethyl acetate (20 mL), treated with 30% K$_2$CO$_3$ to pH 11, and stirred for 30 minutes. The organic layer was washed with 5% NaCl (2×10 mL), filtered, and concentrated. The concentrate was triturated with 1:1 hot ethyl acetate:heptane for 1 hour, cooled to room temperature over 18 hours, and filtered. The solid was dried under vacuum to provide 780 mg (91%) of the desired product. MS m/z 637 (M+H)$^+$; $^1$H NMR (300 MHz, CDCl$_3$) δ 5.72 (br s, 1H), 5.12–4.94 (m, 3H), 4.59 (d, J=7.3 Hz, 1H), 4.35 (d, J=7 Hz, 1H), 3.87 (s, 1H), 3.77–3.55 (m, 4H), 3.07–2.93 (m, 1H), 2.86 (m, 1H), 2.64–2.52 (m, 2H), 2.36 (t, J=3 Hz, 1H), 2.31 (br s, 6H), 2.00–1.86 (m, 2H), 1.62–1.40 (m, 8H), 1.35–1.28 (m, J=6.6 Hz, 3H), 1.17–1.08 (m, 4H), 0.96 (d, J=7 Hz, 3H), 0.85 (t, J=7 Hz, 3H); Anal. calcd for C$_{33}$H$_{52}$N$_2$O$_4$: C, 62.18; H, 8.16; N, 4.40. Found: C, 62.38; H, 8.18; N, 4.12.

EXAMPLE 9

2-(5-Bromo-2-thienyl)pyridine

A solution of 2-thienylpyridine (1.924 kg) and N-bromosuccinimide (2.759 kg) in tert-butyl methyl ether (20.0 kg) was agitated for 15 minutes, treated with 30% HBr in acetic acid (125 g), heated to 35° C. for about 6 hours, and filtered. The wetcake was washed with tert-butyl methyl ether (12.6 kg) while maintaining the temperature of the filtrate at 30° C. to 35° C. The filtrate was washed with 5% Na$_2$SO$_3$ (21 kg) and 10% Na$_2$CO$_3$ (22 kg), concentrated to about 20 L, and diluted with isopropanol (11 kg), which caused the product to crystallize. This procedure was repeated twice more, when NMR analysis of the mother liquor indicated absence of tert-butyl methyl ether. The suspension was concentrated to about 12 L, cooled to 0° C., and filtered. The wetcake was washed with chilled (0° C.) isopropanol (7 kg) and dried in a vacuum oven with a nitrogen purge at 60° C. to provide 2.34 kg (82%) of the desired product. MS m/z 241 (M+H)$^+$; $^1$H NMR δ 8.53 (m, 1H), 7.68 (m, 1H), 7.57 (m, 1H), 7.30 (m, 1H), 7.15 (m, 1H), 7.06 (m, 1H); Anal. calcd for C$_9$H$_6$BrNS: C, 45.01; H, 2.50; N, 5.83. Found: C, 45.14; H, 2.45; N, 5.72.

EXAMPLE 10

Compound of Formula (V-c): R$^4$ and R$^5$ are —C(O)C$_6$H$_5$

A mixture of Example 5 (80.4 g), Example 9 (21.1 kg), palladium acetate (0.179 g), triphenylphosphine (0.418 g), CuI (0.304 g), and triethylamine (200 g) in acetonitrile (424 g) was agitated for 15 minutes, purged with nitrogen and vacuum for 15 minutes, heated to 71–72° C. for 16 hours, treated with isopropyl acetate (1.4 kg), and filtered through diatomeceous earth (Celite®). The filtrate was washed sequentially with 8% NH$_4$Cl (0.8 kg), 10% NaHCO$_3$ (0.8 kg) and saturated NaCl (0.8 kg), concentrated to about 200 g, and diluted with isopropyl acetate (900 g); it was then heated to 70° C., held at that temperature for 1 hour, cooled to about 55° C., heated to 70° C., cooled to about 55° C., heated to 70° C. and cooled slowly to room temperature to provide crystalline desired product. After filtration, the product was washed with chilled isopropyl alcohol until the supernatant was nearly colorless and dried in a vacuum oven with a nitrogen purge at 50° C. to provide 81.5 g (87.5%) of the desired. MS m/z 1165 (M+H)$^+$; $^1$H NMR δ 8.53 (m, 1H), 8.05 (m, 4H), 7.61 (m, 4H), 7.45 (m, 5H), 7.33 (d, 1H), 7.12 (m, 2H), 5.78 (s, 1H), 5.06 (m, 5H), 4.46 (m, 1H), 4.22 (q, 2H), 3.87 (m, 1H), 3.76 (d, 1H), 3.57 (d, 1H), 3.53 (s, 3H), 2.96 (m, 1H), 2.85 (m, 1H), 2.75 (m, 1H), 2.61 (m, 1H), 2.51 (d, 1H), 2.32 (s, 6H), 1.75 (m, 7H), 1.42 (m, 4H), 1.32 (m, 4H), 1.21 (m, 9H), 1.13 (m, 6H), 0.95 (d, 3H), 0.78 (m, 6H). Anal. calcd for $C_{64}H_{82}N_3O_{15}S$: C, 65.98; H, 6.96; N, 3.61. Found: C, 65.76; H, 7.06; N, 3.48.

EXAMPLE 11

Compound of Formula (VII-d): $R^4$ is —$C(O)C_6H_5$

The desired product was prepared in 80% yield by substituting Example 7 for Example 5 in Example 10. MS m/z 900 (M+H)$^+$; $^1$H NMR δ 8.6 (m, 1H), 8.05 (m, 2H), 7.65 (m, 3H), 7.5 (m, 2H), 7.3 (m, 2H), 7.2 (m, 1H), 5.72 (s, 1H), 5.2 (m, 1H), 5.1 (dd, 1H), 4.65 (d, 1H, J=7.5 Hz), 4.5 (d, 1H, J=6 Hz), 3.9 (m, 2H), 3.7 (m, 2H), 3.1 (m, 1H), 2.85 (m, 1H), 2.5 (s, 6H), 1.9 (m, 1H), 1.5 (m, 9H), 1.3 (m, 8H), 1.1 (m, 6H), (m, 6H); Anal. Calcd for $C_{49}H_{61}N_3O_{11}S$: C, 65.39; H, 6.83; N, 4.67. Found: C, 65.16; H, 6.89; N, 4.52.

EXAMPLE 12

Compound of Formula (VI-a): $R^4$ is —$C(O)C_6H_5$

The desired product was prepared in 95% yield by substituting Example 10 for Example 5 in Example 6. MS m/z 902 (M+H)$^+$; $^1$H NMR δ 8.53 (m, 1H), 8.17 (m, 2H), 7.68 (m, 4H), 7.45 (m, 2H), 7.25 (s, 1H), 7.15 (m, 1H), 5.75 (s, 1H), 5.2 (dd, 1H), 5.05 (dd, 1H), 4.8 (d, 1H, J=9Hz), 4.12 (q, 1H, J=7.5Hz), 4.02 (m, 3H), 3.8 (m, 2H), 3.55 (m, 1H), 2.75 (m, 4H), 2.27 (s, 6H), 1.6–2.1 (m, 8H), 1.4 (m, 2H), 1.2 (m, 11H), 1.10 (m, 6H), 0.82 (t, 3H, J=7 Hz), 0.73 (d, 3H, J=7 Hz); Anal. calcd for $C_{49}H_{63}N_3O_{11}S$: C, 65.25; H, 6.98; N, 4.66. Found: C, 64.96; H, 7.04; N, 4.50.

EXAMPLE 13

Compound of Formula (VII-d): $R^4$ is —$C(O)C_6H_5$

A solution of Example 12 (41.3 g) in THF (270 mL) was treated with dimethylsulfide (7.15 g) and diisopropylethylamine (8.8 g), cooled to about –13° C., treated with a solution of N-chlorosuccinimide (13.3 g) in THF (235 mL) between –11° C. and –13° C., stirred at –15° C.±5° C. for about 3 hours, treated sequentially with ethyl acetate (450 mL) and 0.5M NaOH (240 mL), warmed to room temperature, and stirred for 1 hour. The organic layer was separated, washed with 5% NaCl (2×300 mL) and water (300 mL), concentrated under vacuum to 280 mL, diluted with ethyl acetate (300 mL) and reconcentrated to 280 mL. The dilution/distillation was repeated, and the solution was treated with heptanes (240 mL) to form a slurry. The slurry was refluxed for 1 hour, cooled to room temperature and stirred for 18 hours to provide crystals. The crystals are filtered, rinsed with 1:1 ethyl acetate/heptane (40 mL) and vacuum dried at 50° C. to provide 37.58 g (91.2%) of the desired product. MS m/z 900 (M+H)$^+$; $^1$H NMR δ 8.6 (m, 1H), 8.05 (m, 2H), 7.65 (m, 3H), 7.5 (m, 2H), 7.3 (m, 2H), 7.2 (m, 1H), 5.72 (s, 1H), 5.2 (m, 1H), 5.1 (dd, 1H), 4.65 (d, 1H, J=7.5 Hz), 4.5 (d, 1H, J=6 Hz), 3.9 (m, 2H), 3.7 (m, 2H), 3.1 (m, 1H), 2.85 (m, 1H), 2.5 (s, 6H), 1.9 (m, 1H), 1.5 (m, 9H), 1.3 (m, 8H), 1.1 (m, 6H), 0.9 (m, 6H); Anal. Calcd for $C_{49}H_{61}N_3O_{11}S$: C, 65.39; H, 6.83; N, 4.67. Found: C, 65.16; H, 6.89; N, 4.52.

EXAMPLE 14

Compound of Formula (VII-d): $R^4$ is Hydrogen

The desired product was prepared in 92% yield by substituting Example 11 or Example 13 for Example 7 in Example 8. MS m/z 796 (M+H)$^+$; $^1$H NMR δ 8.58 (m, 1H), 7.63 (m, 2H), 7.45 (d, 1H, J=7 Hz), 7.32 (d, 1H, J=6 Hz), 7.15 (m, 1H), 5.73 (s, 1H), 5.15 (m, 1H), 4.43 (m, 3H), 4.0 (m, 4H), 3.6 (m, 1H), 3.42 (m, 1H), 3.2 (m, 1H), 3.1 (m, 1H), 2.97 (m, 1H), 2.62 (s, 6H), 1.95 (m, 2H), 1.7 (m, 2H), 1.5 (m, 8H), 1.4 (m, 8H), 1.3 (m, 3H), 1.2 (m, 6H), 0.9 (m, 3H); Anal. calcd for $C_{42}H_{57}N_3O_{10}S$: C, 63.37; H, 7.22; N, 5.28 Found: C, 63.19; H, 7.28; N, 5.12.

It will be evident to one skilled in the art that this invention is not limited to the forgoing examples, and that it can be embodied in other specific forms without departing from the essential attributes thereof. Thus, it is desired that the examples be considered as illustrative and not restrictive, reference being made to the claims, and that all changes which come within the meaning and range of equivalency of the claims be embraced therein.

What is claimed is:

1. A process for preparing a compound of formula (IV)

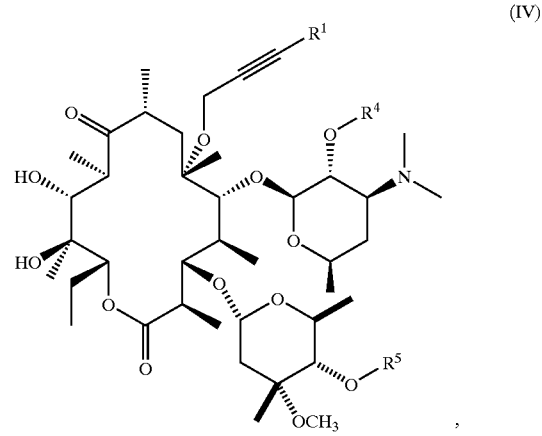

(IV)

wherein
$R^1$ is hydrogen or optionally substituted furanyl, thienyl, pyrrolyl, oxazolyl, thiazolyl, imidazolyl, isoxazolyl, isothiazolyl, oxadiazolyl, triazolyl, thiadiazolyl, pyridyl, pyridazinyl, pyrimidinyl, pyrazinyl, pyrazolyl, or triazinyl,
and
$R^4$ and $R^5$ are independently hydrogen or a hydroxyl protecting group;
the process comprising:
(a) simultaneously reacting a compound of formula (I)

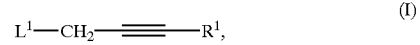

(I)

wherein
$L^1$ is selected from the group consisting of halo, trifluoromethanesulfonyl, and optionally substituted phenylsulfonyl; and $R^1$ is hydrogen or optionally substituted furanyl, thienyl, pyrrolyl, oxazolyl, thiazolyl, imidazolyl, isoxazolyl, isothiazolyl, oxadiazolyl, triazolyl, thiadiazolyl, pyridyl, pyridazinyl, pyrimidinyl, pyrazinyl, pyrazolyl, or triazinyl, a compound of formula (II)

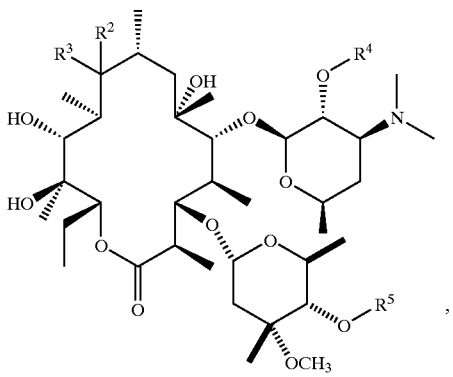

(II)

wherein $R^2$ and $R^3$ are taken together and are selected from the group consisting of =N—O—$R^6$, =N—O—C(O)—$R^6$, =N—O—C($R^{7a}$)($R^{7b}$)—O$R^8$, =N—O—Si($R^9$)$_3$, =N—N($R^{10a}$)($R^{10b}$), and =N—N=C($R^{11a}$)($R^{11b}$);

$R^4$ and $R^5$ are independently hydrogen or a hydroxyl protecting group;

$R^6$ is selected from the group consisting of alkyl, cycloalkyl, cycloalkylalkyl, phenyl, and phenylalkyl;

$R^{7a}$ and $R^{7b}$ are independently selected from the group consisting of hydrogen, alkyl, cycloalkyl, cycloalkylalkyl, phenyl, and phenylalkyl;

$R^8$ is selected from the group consisting of alkyl, cycloalkyl, cycloalkylalkyl, phenyl, and phenylalkyl; or $R^{7a}$ and $R^{7b}$ together or $R^{7a}$ and $R^8$ together are alkylene;

each $R^9$ is independently selected from the group consisting of alkyl, cycloalkyl, cycloalkylalkyl, phenyl, and phenylalkyl;

$R^{10a}$ and $R^{10b}$ are independently selected from the group consisting of alkyl, cycloalkyl, cycloalkylalkyl, phenyl, phenylalkyl, and a nitrogen-protecting group; or $R^{10a}$ and $R^{10b}$ together are alkylene; and $R^{11a}$ and $R^{11b}$ are independently selected from the group consisting of hydrogen, alkyl, cycloalkyl, cycloalkylalkyl, phenyl, and phenylalkyl; or $R^{11a}$ and $R^{11b}$ together are alkylene, and an alkoxide base to provide a compound of formula (III)

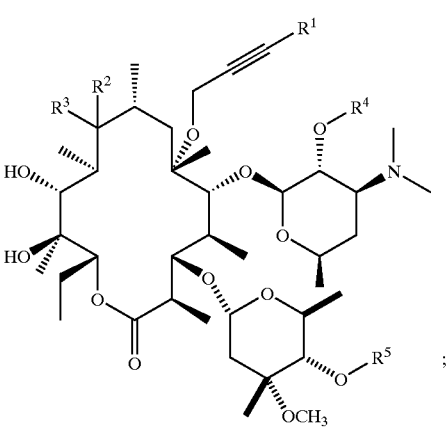

(III)

and (b) reacting the product of step (a) with a first acid and sodium nitrite at a pressure of about 30 psi to about 70 psi.

2. The process of claim 1 wherein, for the compound of formula (I), $L^1$ is bromide; and $R^1$ is hydrogen.

3. The process of claim 1 wherein, for the compound of formula (II), $R^2$ and $R^3$ together are =N—O—C($R^{7a}$)($R^{7b}$)—O$R^8$;

$R^4$ and $R^5$ are —C(O)$C_6H_5$;

$R^{7a}$ and $R^{7b}$ are together and are pentylene; and $R^8$ is isopropyl.

4. The process of claim 1 wherein, for the compound of formula (III), $R^1$ is hydrogen;

$R^2$ and $R^3$ together are =N—O—C($R^{7a}$)($R^{7b}$)—O$R^8$;

$R^4$ and $R^5$ are —C(O)$C_6H_5$;

$R^{7a}$ and $R^{7b}$ are together and are pentylene; and $R^8$ is isopropyl.

5. The process to claim 1 wherein, for the compound of formula (IV), $R^1$ is hydrogen; and $R^4$ and $R^5$ are —C(O)$C_6H_5$.

6. The process of claim 1, wherein the alkoxide base is selected from the group consisting of lithium methoxide, lithium ethoxide, lithium iso-propoxide, lithium tert-butoxide sodium methoxide, sodium ethoxide, sodium iso-propoxide, sodium tert-butoxide, potassium methoxide, potassium ethoxide, potassium iso-propoxide, and potassium tert-butoxide.

7. The process of claim 6, wherein the alkoxide base is potassium tert-butoxide.

8. The process of claim 1, wherein the first acid is selected from the group consisting of hydrochloric, hydrobromic, hydroiodic, trifluoroacetic, methanesulfonic, and para-toluenesulfonic.

9. The process of claim 8, wherein the first acid is hydrochloric.

10. The process of claim 9, wherein the hydrochloric acid is present in about 5 to about 10 molar equivalents per molar equivalent of the compound of formula (III), and the sodium nitrite is present in about 5 to about 8 molar equivalents per molar equivalent of the compound of formula (III).

11. The process of claim 10, wherein the hydrochloric acid is present in about 8 molar equivalents per molar equivalent of the compound of formula (III).

12. The process of claim 10, wherein the sodium nitrite is present in about 7.5 molar equivalents per molar equivalent of the compound of formula (III).

13. The process of claim 1 which is conducted as a continuous process.

14. The process of claim 1, wherein step (a) is conducted at a temperature of about 0° C. to about 5° C.

15. The process of claim 1, wherein step (b) is conducted at a temperature of about 20° C. to about 40° C.

16. The process of claim 1, wherein step (a) is conducted over about 2.5 to about 4 hours.

17. The process of claim 16, wherein step (a) is conducted in a mixture of tetrahydrofuran and dimethylsulfoxide.

18. The process of claim 1, wherein step (b) is conducted in a solvent selected from the group consisting of water, a $C_1$–$C_6$ alcohol, and mixtures thereof.

19. The process of claim 1, wherein step (b) is conducted in a mixture of water and ethanol.

20. A process for preparing a compound of formula (IV-a)

(IV-a)
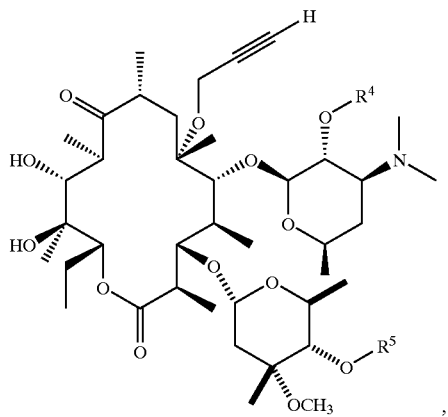

wherein
R$^4$ and R$^5$ are hydroxyl protecting groups;
the process comprising:
(a) simultaneously reacting 3-bromo-1-propyne, a compound of formula (II)

(II)
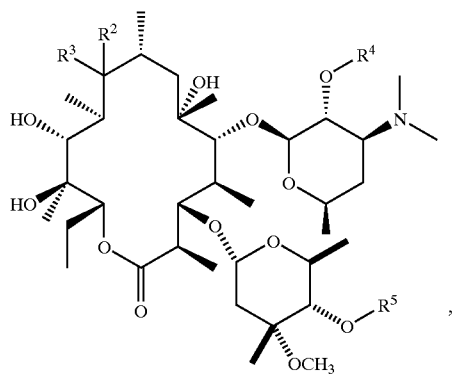

wherein
R$^2$ and R$^3$ together are =N—O—C(R$^{7a}$)(R$^{7b}$)—OR$^8$;
R$^4$ and R$^5$ are hydroxyl protecting groups;
R$^{7a}$ and R$^{7b}$ are together and are pentylene; and
R$^8$ is isopropyl,
and potassium tert-butoxide over about 2.5 to about 4 hours to provide a compound of formula (III-b)

(III-b)
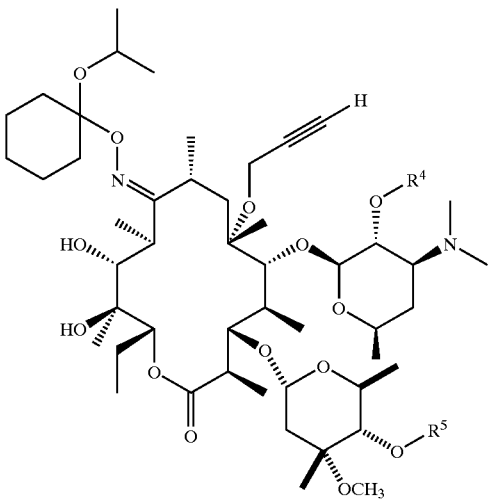

wherein
R$^4$ and R$^5$ are hydroxyl protecting groups;
and
(b) reacting the product of step (a) with about 5 to about 10 molar equivalents of hydrochloric acid per molar equivalent of the compound of formula (III-b) and about 5 to about 8 molar equivalents of sodium nitrite per molar equivalent of the compound of formula (III-b) at a pressure of about 15 psi to about 70 psi.

21. A process for preparing a compound of formula (IV-a)

(IV-a)
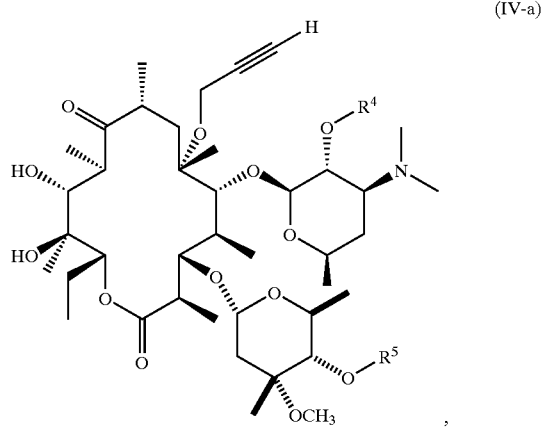

wherein
R$^4$ and R$^5$ are hydroxyl protecting groups;
the process comprising:
(a) simultaneously reacting 3-bromo-1-propyne, a compound of formula (II)

(II)
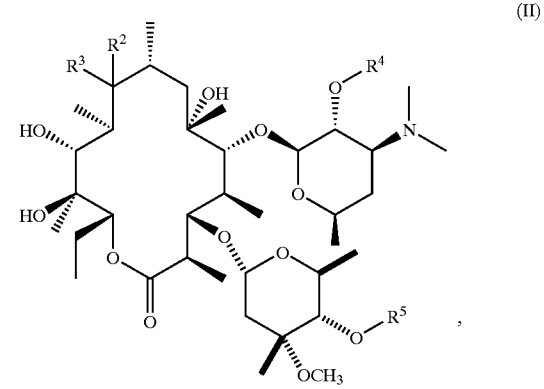

wherein
R$^2$ and R$^3$ together are =N—O—C(R$^{7a}$)(R$^{7b}$)—OR$^8$;
R$^4$ and R$^5$ are hydroxyl protecting groups;
R$^{7a}$ and R$^{7b}$ together are pentylene; and
R$^8$ is isopropyl, and potassium tert-butoxide, in a mixture of tetrahydrofuran and dimethylsulfoxide, at a temperature between about 0° C. to about 5° C., to provide a compound of formula (II-b)

(III-b)

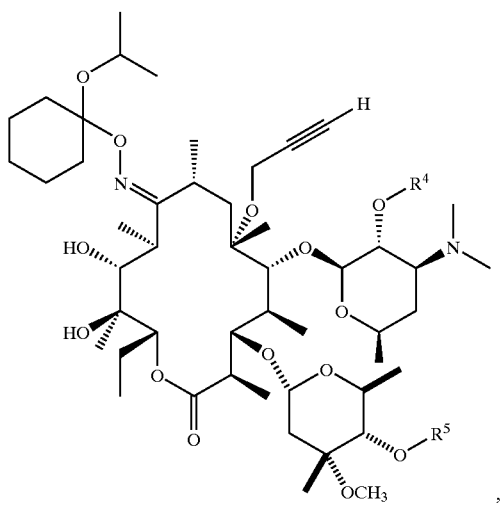

wherein
$R^4$ and $R^5$ are hydroxyl protecting groups; and
(b) reacting the product of step (a) with about 7 to about 10 molar equivalents of hydrochloric acid and about 5 to about 8 molar equivalents of sodium nitrite per equivalent of the compound of formula (III-b), in a mixture of water and ethanol, at a temperature of about 20° C. to about 40° C., and at a pressure of about 15 psi to about 70 psi.

22. A process for preparing compounds of formula (V-b)

(V-b)

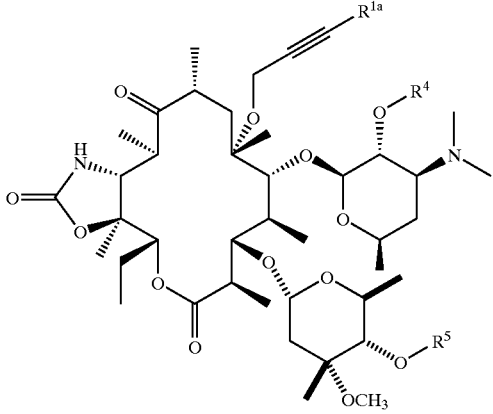

and compounds of formula (VII-b)

(VII-b)

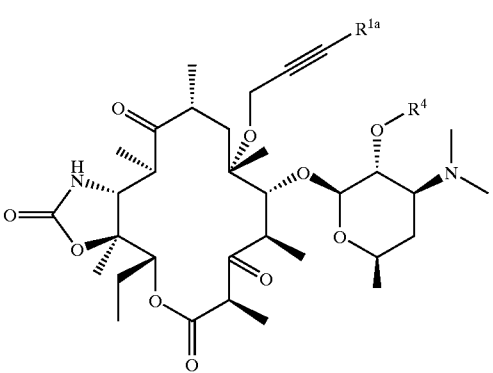

wherein, for compounds of formulas (V-b) and (VII-b),
$R^{1a}$ is optionally substituted furanyl, thienyl, pyrrolyl, oxazolyl, thiazolyl, imidazolyl, isoxazolyl, isothiazolyl, oxadiazolyl, triazolyl, thiadiazolyl, pyridyl, pyridazinyl, pyrimidinyl, pyrazinyl, pyrazolyl, or triazinyl, and
$R^4$ and $R^5$ are independently hydrogen or a hydroxyl protecting group,
the process comprising:
(a) reacting a compound of formula (V-a)

(V-a)

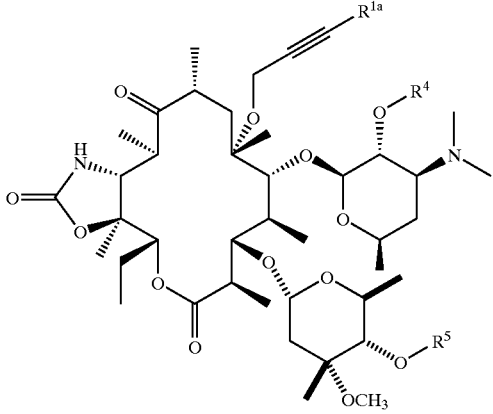

or a compound of formula (VII-a)

(VII-a)

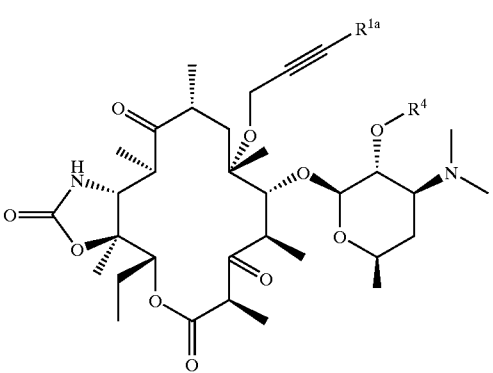

with a compound of formula $L^1$, —$R^{1a}$ wherein
$L^1$ is selected from the group consisting of halo, trifluoromethanesulfonyl, and optionally substituted phenylsulfonyl,
a palladium catalyst, an additive and a first base; and
(b) optionally deprotecting the product of step (a).

23. The process of claim 22, wherein $R^{1a}$ is

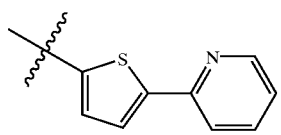

24. The process of claim 22, wherein the palladium catalyst is selected from the group consisting of optionally supported palladium(0), palladium(0) complexes, palladium (II) salts, and palladium(II) complexes.

25. The process of claim 24, wherein the palladium catalyst is palladium acetate.

26. The process of claim 22, wherein the additive is selected from the group consisting of monodentate phosphorus-containing ligands and bidentate phosphines.

27. The process of claim 26, wherein the additive is triphenylphosphine.

28. The process of claim 22, wherein the first base is selected from the group consisting of trialkylamines, imidazole, pyridine, pyridazine, pyrimidine, pyrazine, and bicyclic amines.

29. The process of claim 28, wherein the first base is triethylamine.

30. The process of claim 22 which is conducted as a continuous process.

31. the process of claim 22, wherein step (a) is conducted at a temperature of about 60° C. to about 80° C.

32. The process of claim 31, wherein step (a) is conducted in an aprotic solvent.

33. The process of claim 32, wherein the aprotic solvent is acetonitrile.

34. The process of claim 21, further comprising
(a) reacting a compound of formula (IV-a)

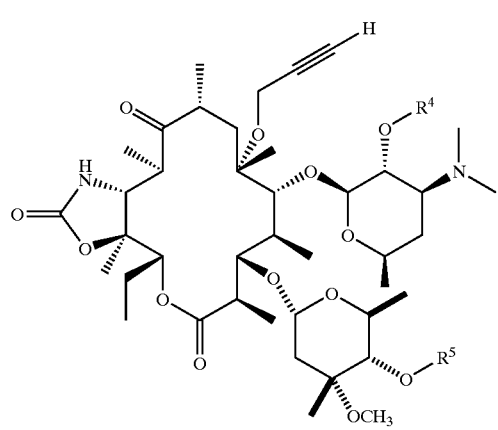

(IV-a)

with 1,1'-carbonyldiimidazole and lithium duisopropylamide, followed by treatment of the product with ammonia and potassium tert-butoxide, to provide a compound of formula (V-a)

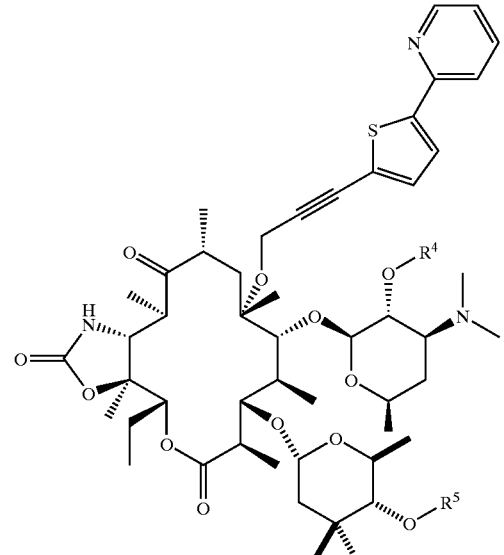

(V-a)

(b) optionally reacting the product of step (a) with hydrochloric acid to provide a compound of formula (VI)

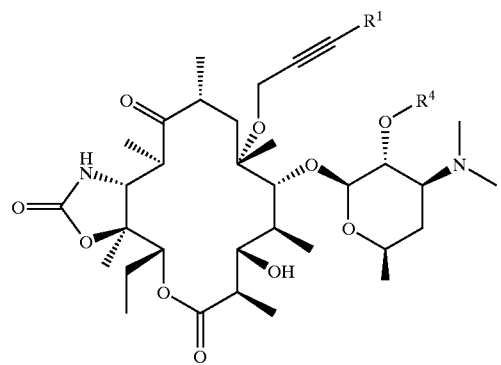

(VI)

wherein
$R^1$ is hydrogen;
and
(c) reacting the product of step (b) with an oxidizing agent.

35. A process for preparing compounds of formula (V-c)

(V-c)

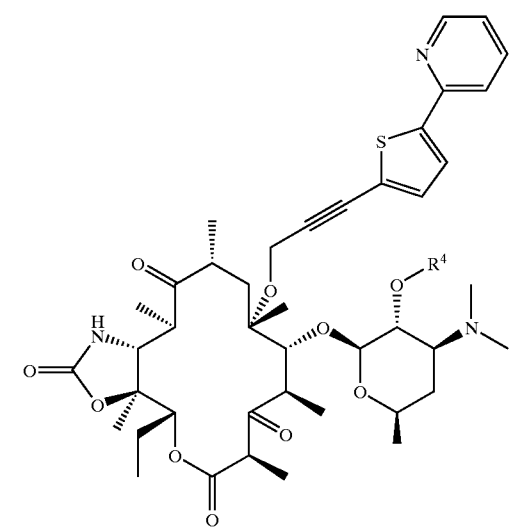

or compounds of formula (Vd-d)

(VII-d)

wherein, for compounds of formulas (V-c) and (VII-d), R⁴ and R⁵ are independently hydrogen or a hydroxyl protecting group, the process comprising:

(a) reacting a compound of formula (V-a)

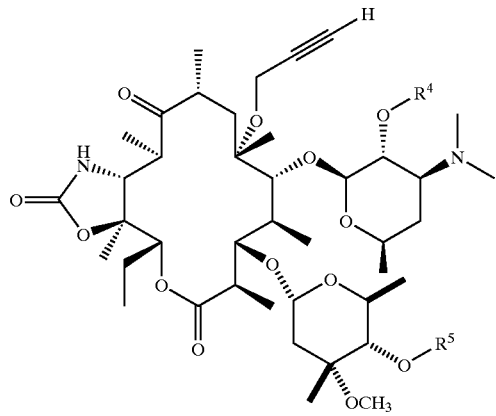
(V-a)

or a compound of formula (VII-a)

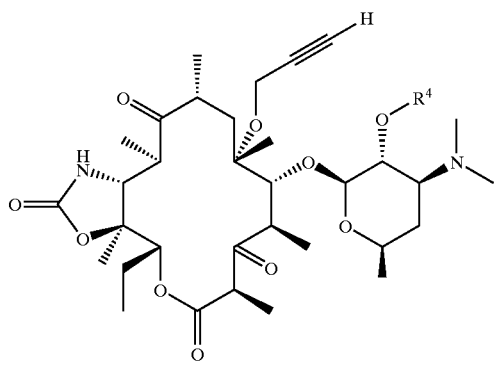
(VII-a)

with 2-(5-bromo-2-thienyl)pyridine, palladium acetate, triphenylphosphine and triethylamine;
and (b) optionally deprotecting the product of step (a).

36. A process for preparing compounds of formula (V-c)

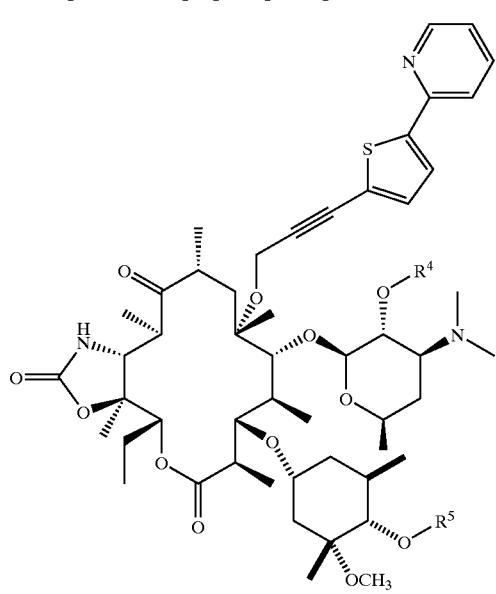
(V-c)

or compounds of formula (VII-d)

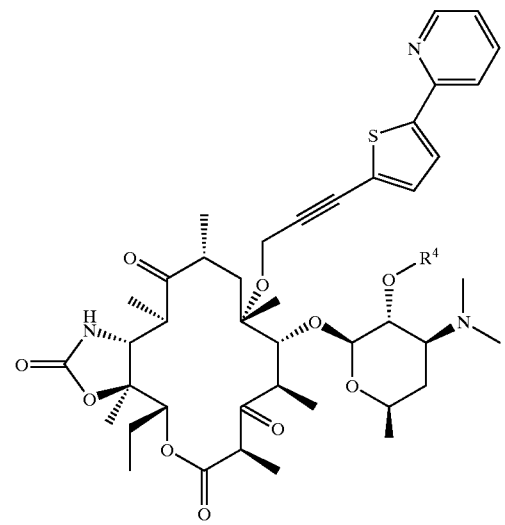
(VII-d)

wherein, for compounds of formulas (V-c) and (VII-d), R⁴ and R⁵ are independently hydrogen or a hydroxyl protecting group, the process comprising:

(a) reacting a compound of formula (V-a)

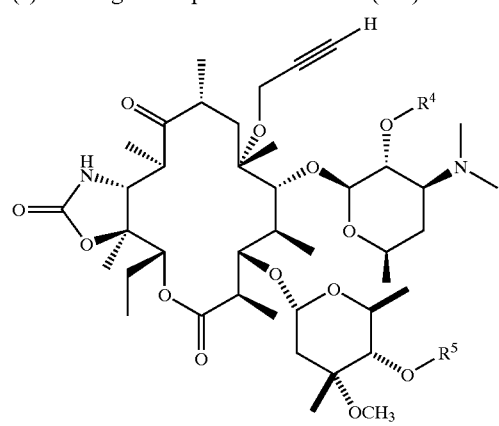
(V-a)

or a compound of formula (VII-a)

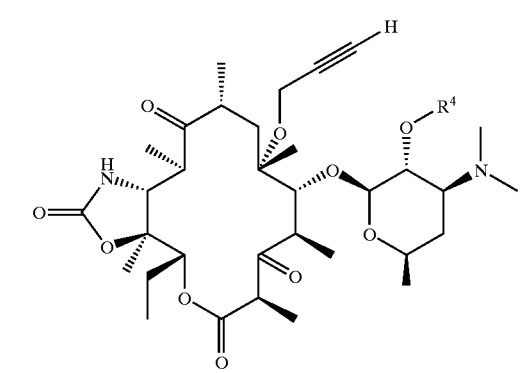
(VII-a)

with 2-(5-bromo-2-thienyl)pyridine, palladium acetate, triphenylphosphine and triethylamine in acetonitrile at a temperature of about 60° C. to about 80° C.;
and (b) optionally deprotecting the product of step (a).

* * * * *

UNITED STATES PATENT AND TRADEMARK OFFICE
CERTIFICATE OF CORRECTION

PATENT NO. : 6,605,707 B1
DATED : August 12, 2003
INVENTOR(S) : Francis A.J. Kerdesky et al.

It is certified that error appears in the above-identified patent and that said Letters Patent is hereby corrected as shown below:

Column 34,
Line 48, replace "$L^1, -R^{1a}$" with -- $L^1-R^{1a}$ --.

Column 35,
Line 44, replace "duisopropylamide" with -- diisopropylamide --.

Signed and Sealed this

Thirteenth Day of July, 2004

JON W. DUDAS
*Acting Director of the United States Patent and Trademark Office*